(12) United States Patent
Lau et al.

(10) Patent No.: US 7,905,832 B1
(45) Date of Patent: Mar. 15, 2011

(54) METHOD AND SYSTEM FOR PERSONALIZED MEDICAL MONITORING AND NOTIFICATIONS THEREFOR

(75) Inventors: Chung Lau, Sunnyvale, CA (US); C. Douglass Thomas, Campbell, CA (US)

(73) Assignee: IpVenture, Inc., Los Altos, CA (US)

( * ) Notice: Subject to any disclaimer, the term of this patent is extended or adjusted under 35 U.S.C. 154(b) by 388 days.

(21) Appl. No.: 10/397,641

(22) Filed: Mar. 26, 2003

Related U.S. Application Data

(60) Provisional application No. 60/444,198, filed on Jan. 30, 2003, provisional application No. 60/418,491, filed on Oct. 15, 2002, provisional application No. 60/404,645, filed on Aug. 19, 2002, provisional application No. 60/375,998, filed on Apr. 24, 2002.

(51) Int. Cl.
*A61B 5/00* (2006.01)

(52) U.S. Cl. ......... 600/300; 128/920; 705/2; 340/573.1

(58) Field of Classification Search .......... 600/300–301; 128/903–906, 920–923; 705/2–4; 701/213
See application file for complete search history.

(56) References Cited

U.S. PATENT DOCUMENTS

| | | | |
|---|---|---|---|
| 5,389,934 A | 2/1995 | Kass | |
| 5,400,020 A | 3/1995 | Jones et al. | |
| 5,461,365 A | 10/1995 | Schlager et al. | |
| 5,491,486 A | 2/1996 | Welles, II et al. | |
| 5,512,902 A | 4/1996 | Guthrie et al. | |
| 5,515,858 A | 5/1996 | Myllymaki | |
| 5,528,247 A | 6/1996 | Nonami | |
| 5,528,518 A | 6/1996 | Bradshaw et al. | |
| 5,539,748 A | 7/1996 | Raith | |
| 5,541,845 A | 7/1996 | Klein | |
| 5,550,551 A | 8/1996 | Alesio | |
| 5,568,119 A | 10/1996 | Schipper et al. | |
| 5,570,412 A | 10/1996 | LeBlanc | |
| 5,576,716 A | 11/1996 | Sadler | |
| 5,592,173 A | 1/1997 | Lau et al. | |
| 5,598,460 A | 1/1997 | Tendler | |
| 5,604,708 A | 2/1997 | Helms et al. | |
| 5,623,260 A | 4/1997 | Jones | |
| 5,629,678 A | 5/1997 | Gargano et al. | |
| 5,652,570 A | 7/1997 | Lepkofker | |
| 5,673,692 A * | 10/1997 | Schulze et al. | ................ 600/301 |
| 5,710,551 A | 1/1998 | Ridgeway | |
| 5,712,619 A | 1/1998 | Simkin | |
| 5,731,757 A | 3/1998 | Layson et al. | |
| 5,731,788 A | 3/1998 | Reeds | |

(Continued)

FOREIGN PATENT DOCUMENTS

EP 0 874 529 A2 10/1998

(Continued)

OTHER PUBLICATIONS

J.Wrolstad, "Chrysler Claims First With Bluetooth Mobile Phone System," Wireless Newsfactor, Oct. 26, 2001.

(Continued)

*Primary Examiner* — Henry M Johnson, III
*Assistant Examiner* — Kai Rajan

(57) ABSTRACT

Improved methods and systems for personal medical monitoring are disclosed. The monitoring yields status information pertaining to persons being monitored. Notifications, recommendations and/or actions can be initiated by examination or analysis of the status information. The status information can include health, position (location) and other information.

39 Claims, 13 Drawing Sheets

U.S. PATENT DOCUMENTS

| | | |
|---|---|---|
| 5,742,233 A | 4/1998 | Hoffman et al. |
| 5,751,245 A | 5/1998 | Janky et al. |
| 5,771,001 A | 6/1998 | Cobb |
| 5,774,876 A | 6/1998 | Woolley et al. |
| 5,797,091 A | 8/1998 | Clise et al. |
| RE35,920 E | 10/1998 | Sorden et al. |
| 5,826,195 A | 10/1998 | Westerlage et al. |
| 5,835,907 A | 11/1998 | Newman |
| 5,841,352 A | 11/1998 | Prakash |
| 5,844,862 A | 12/1998 | Cocatre-Zilgien |
| 5,850,196 A | 12/1998 | Mowers |
| 5,861,841 A | 1/1999 | Gildea et al. |
| 5,883,594 A | 3/1999 | Lau |
| 5,889,770 A | 3/1999 | Jokiaho et al. |
| 5,905,461 A | 5/1999 | Neher |
| 5,948,043 A | 9/1999 | Mathis |
| 5,959,575 A | 9/1999 | Abbott |
| 5,959,577 A | 9/1999 | Fan et al. |
| 5,963,130 A | 10/1999 | Schlager et al. |
| 5,982,285 A | 11/1999 | Bueche et al. |
| 5,991,690 A | 11/1999 | Murphy |
| 5,995,849 A | 11/1999 | Williams et al. |
| 6,002,363 A | 12/1999 | Krasner |
| 6,002,982 A | 12/1999 | Fry |
| 6,009,319 A | 12/1999 | Khullar et al. |
| 6,013,007 A | 1/2000 | Root et al. |
| 6,014,080 A | 1/2000 | Layson, Jr. |
| 6,014,090 A | 1/2000 | Rosen et al. |
| 6,023,241 A | 2/2000 | Clapper |
| 6,032,051 A | 2/2000 | Hall et al. |
| 6,034,622 A | 3/2000 | Levine |
| 6,054,928 A | 4/2000 | Lemelson |
| 6,064,336 A | 5/2000 | Krasner |
| 6,067,018 A | 5/2000 | Skelton et al. |
| 6,067,044 A | 5/2000 | Whelan et al. |
| 6,072,396 A | 6/2000 | Gaukel |
| 6,078,290 A | 6/2000 | McBurney et al. |
| 6,083,248 A | 7/2000 | Thompson |
| 6,083,353 A | 7/2000 | Alexander |
| 6,094,168 A | 7/2000 | Duffett-Smith et al. |
| 6,100,806 A | 8/2000 | Gaukel |
| 6,131,067 A | 10/2000 | Girerd et al. |
| 6,141,570 A | 10/2000 | O'Neill, Jr. et al. |
| 6,144,303 A | 11/2000 | Federman |
| 6,148,280 A | 11/2000 | Kramer |
| 6,163,696 A | 12/2000 | Bi et al. |
| 6,171,264 B1 | 1/2001 | Bader |
| 6,172,640 B1 | 1/2001 | Durst et al. |
| 6,175,616 B1 | 1/2001 | Light et al. |
| 6,198,390 B1 | 3/2001 | Schlager et al. |
| 6,198,431 B1 | 3/2001 | Gibson |
| 6,198,930 B1 | 3/2001 | Schipper |
| 6,199,045 B1 | 3/2001 | Giniger et al. |
| 6,226,622 B1 | 5/2001 | Dabbiere |
| 6,231,519 B1 * | 5/2001 | Blants et al. .................. 600/300 |
| 6,232,916 B1 | 5/2001 | Grillo et al. |
| 6,236,358 B1 | 5/2001 | Durst et al. |
| 6,238,337 B1 | 5/2001 | Kambhatla et al. |
| 6,243,039 B1 | 6/2001 | Elliot |
| 6,243,660 B1 | 6/2001 | Hsu et al. |
| 6,246,376 B1 | 6/2001 | Bork et al. |
| 6,263,280 B1 | 7/2001 | Stingone, Jr. |
| 6,278,936 B1 | 8/2001 | Jones |
| 6,282,362 B1 | 8/2001 | Murphy et al. |
| 6,292,687 B1 | 9/2001 | Lowell et al. |
| 6,298,306 B1 | 10/2001 | Suarez et al. |
| 6,300,875 B1 | 10/2001 | Schafer |
| 6,302,844 B1 * | 10/2001 | Walker et al. .................. 600/300 |
| 6,314,308 B1 | 11/2001 | Sheynblat et al. |
| 6,317,049 B1 | 11/2001 | Toubia et al. |
| 6,323,807 B1 | 11/2001 | Golding et al. |
| 6,324,213 B1 | 11/2001 | Harrison |
| 6,327,533 B1 | 12/2001 | Chou |
| 6,331,817 B1 | 12/2001 | Goldberg |
| 6,339,397 B1 | 1/2002 | Baker |
| 6,340,928 B1 | 1/2002 | McCurdy |
| 6,342,847 B1 | 1/2002 | Archuleta et al. |
| 6,349,257 B1 | 2/2002 | Liu et al. |
| 6,353,390 B1 | 3/2002 | Beri et al. |
| 6,353,798 B1 | 3/2002 | Green et al. |
| 6,356,841 B1 | 3/2002 | Hamrick et al. |
| 6,362,778 B2 | 3/2002 | Neher |
| 6,363,254 B1 | 3/2002 | Jones et al. |
| 6,363,323 B1 | 3/2002 | Jones |
| 6,373,430 B1 | 4/2002 | Beason et al. |
| 6,377,810 B1 | 4/2002 | Geiger |
| 6,388,612 B1 | 5/2002 | Neher |
| 6,404,352 B1 | 6/2002 | Ichikawa et al. |
| 6,407,698 B1 | 6/2002 | Ayed |
| 6,411,892 B1 | 6/2002 | Van Diggelen |
| 6,411,899 B2 | 6/2002 | Dussell et al. |
| 6,421,538 B1 | 7/2002 | Byrne |
| 6,426,719 B1 | 7/2002 | Nagareda et al. |
| 6,427,120 B1 | 7/2002 | Garin et al. |
| 6,430,602 B1 | 8/2002 | Kay et al. |
| 6,433,732 B1 | 8/2002 | Dutta et al. |
| 6,434,396 B1 | 8/2002 | Rune |
| 6,441,778 B1 | 8/2002 | Durst et al. |
| 6,442,380 B1 | 8/2002 | Mohindra |
| 6,443,890 B1 * | 9/2002 | Schulze et al. ................. 600/300 |
| 6,445,937 B1 | 9/2002 | daSilva |
| 6,453,237 B1 | 9/2002 | Fuchs et al. |
| 6,466,821 B1 | 10/2002 | Planca et al. |
| 6,469,639 B2 | 10/2002 | Tanenhaus et al. |
| 6,471,087 B1 | 10/2002 | Shusterman |
| 6,478,736 B1 * | 11/2002 | Mault ........................... 600/300 |
| 6,505,048 B1 | 1/2003 | Moles et al. |
| 6,513,532 B2 * | 2/2003 | Mault et al. .................... 128/921 |
| 6,522,871 B1 | 2/2003 | Patrick et al. |
| 6,522,889 B1 | 2/2003 | Aarnio |
| 6,529,164 B1 | 3/2003 | Carter |
| 6,544,193 B2 * | 4/2003 | Abreu ........................... 600/558 |
| 6,552,652 B2 | 4/2003 | Beken |
| 6,559,620 B2 | 5/2003 | Zhou et al. |
| 6,569,094 B2 | 5/2003 | Suzuki et al. |
| 6,579,231 B1 * | 6/2003 | Phipps ........................... 600/300 |
| 6,579,844 B1 * | 6/2003 | Morrison et al. ............... 510/445 |
| 6,625,437 B1 | 9/2003 | Jampolsky et al. |
| 6,630,885 B2 | 10/2003 | Hardman et al. |
| 6,640,085 B1 | 10/2003 | Chatzipetros et al. |
| 6,650,907 B1 | 11/2003 | Kamperschroer et al. |
| 6,679,071 B1 | 1/2004 | Storey et al. |
| 6,721,542 B1 | 4/2004 | Anttila et al. |
| 6,747,675 B1 | 6/2004 | Abbott et al. |
| 6,788,766 B2 | 9/2004 | Logan |
| 6,804,606 B2 | 10/2004 | Jones |
| 6,847,892 B2 * | 1/2005 | Zhou et al. .................... 701/213 |
| 6,856,804 B1 | 2/2005 | Ciotta |
| 6,865,385 B1 | 3/2005 | Kohda et al. |
| 6,937,900 B1 | 8/2005 | Planca et al. |
| 6,952,645 B1 | 10/2005 | Jones |
| 6,975,941 B1 | 12/2005 | Lau et al. |
| 6,980,826 B2 | 12/2005 | Yamaguchi |
| 7,071,842 B1 | 7/2006 | Brady, Jr. |
| 7,085,253 B2 | 8/2006 | Yang |
| 7,136,832 B2 | 11/2006 | Li et al. |
| 7,212,829 B1 | 5/2007 | Lau et al. |
| 7,218,938 B1 | 5/2007 | Lau et al. |
| 7,253,731 B2 | 8/2007 | Joao |
| 7,321,774 B1 | 1/2008 | Lau et al. |
| 7,325,061 B2 | 1/2008 | Haruki |
| 7,366,522 B2 | 4/2008 | Thomas |
| 7,403,972 B1 | 7/2008 | Lau et al. |
| 2001/0006891 A1 | 7/2001 | Cho |
| 2001/0020204 A1 | 9/2001 | Runyon et al. |
| 2001/0027378 A1 | 10/2001 | Tennison et al. |
| 2001/0028304 A1 | 10/2001 | I'Anson et al. |
| 2001/0044299 A1 | 11/2001 | Sandegren |
| 2001/0052849 A1 | 12/2001 | Jones, Jr. |
| 2002/0000930 A1 | 1/2002 | Crowson et al. |
| 2002/0016173 A1 | 2/2002 | Hunzinger |
| 2002/0027507 A1 | 3/2002 | Yarin et al. |
| 2002/0038182 A1 | 3/2002 | Wong et al. |
| 2002/0050945 A1 | 5/2002 | Tsukishima et al. |
| 2002/0057192 A1 | 5/2002 | Eagleson et al. |
| 2002/0063622 A1 | 5/2002 | Armstrong et al. |
| 2002/0071677 A1 | 6/2002 | Sumanaweera |

| | | | |
|---|---|---|---|
| 2002/0077080 | A1 | 6/2002 | Greene |
| 2002/0087260 | A1 | 7/2002 | Hancock et al. |
| 2002/0087619 | A1 | 7/2002 | Tripathi |
| 2002/0094067 | A1 | 7/2002 | August |
| 2002/0111171 | A1 | 8/2002 | Boesch et al. |
| 2002/0111819 | A1 | 8/2002 | Li et al. |
| 2002/0115453 | A1 | 8/2002 | Poulin et al. |
| 2002/0119789 | A1 | 8/2002 | Friedman |
| 2002/0193121 | A1 | 12/2002 | Nowak et al. |
| 2003/0003943 | A1 | 1/2003 | Bajikar |
| 2003/0009410 | A1 | 1/2003 | Ramankutty et al. |
| 2003/0013445 | A1 | 1/2003 | Fujiwara et al. |
| 2003/0069759 | A1 | 4/2003 | Smith |
| 2003/0151507 | A1 | 8/2003 | Andre et al. |
| 2003/0204132 | A1* | 10/2003 | Suzuki et al. ............ 600/300 |
| 2004/0034470 | A1 | 2/2004 | Workman |
| 2004/0046637 | A1 | 3/2004 | Wesby Van Swaay |
| 2004/0114731 | A1 | 6/2004 | Gillett et al. |
| 2004/0117108 | A1 | 6/2004 | Nemeth |
| 2004/0233065 | A1 | 11/2004 | Freeman |
| 2006/0173444 | A1 | 8/2006 | Choy et al. |
| 2008/0021645 | A1 | 1/2008 | Lau et al. |
| 2009/0042540 | A1 | 2/2009 | Bodnar et al. |

FOREIGN PATENT DOCUMENTS

| | | |
|---|---|---|
| EP | 1 037 447 A2 | 9/2000 |
| WO | WO 97/41654 | 11/1997 |
| WO | WO 98/01769 A1 | 1/1998 |
| WO | WO 98/16045 | 4/1998 |
| WO | WO 00/51391 | 8/2000 |
| WO | WO 01/50151 A1 | 7/2001 |
| WO | WO 02/42979 A1 | 5/2002 |
| WO | WO 02/084618 A1 | 10/2002 |
| WO | WO 03/012720 A1 | 2/2003 |

OTHER PUBLICATIONS

K. Miyake, "Sharp to unveil 3G PDA-type cell phone," ITworld.com, Inc., Jan. 11, 2002.

"Audiovox Intros GPS, Bluetooth Phone;" INT Media Group, Inc. (allNetDevices), Apr. 5, 2002. (downloaded: www.allnetdevices.com/wireless/news/2001/1/15/audiovox_intros.html).

"Start-up crams single chip with phone, GPS and Bluetooth," CNET Network, Inc. (ZDNET), Mar. 22, 2002 (downloaded: http://news.zdnet.co.uk/story/0,t284-x2107163,00.html).

"Fleet Management Systems-Asset Tracking Devices," Axiom Navigation Inc., 2000-2001 (downloaded Oct. 19, 2002: www.axiomnav.com/Prod_Systems/prod_system.asp).

"Global Cell Phone Location," Axiom Navigation Inc., 2000-2001 (downloaded Oct. 19, 2002: www.axiomnav.com/Prod_Global/prod_global.asp).

"X-GPS™—Hybrid GPS Location Server Solution," Axiom Navigation Inc., 2000-2001 (downloaded Oct. 19, 2002: www.axiomnav.com/Prod_Global/x-gps.asp).

"Digital/Analog Compass Sensors" and "1655 Digital Compass Sensor," webpages, The Robson Company, Inc., pp. 1-2 (downloaded Apr. 11, 2002: www.dinsmoresensors.com/index.html).

Delphi and MobileAria Demonstrate True Hands Free In-Vehicle Mobile Productivity Services At CES, Press Release, Delphi Automotive Systems, Jan. 8, 2002 (downloaded Apr. 5, 2002: www.delphiauto.com/news/pressRelease/pr6828-01082002).

"NavMate® Navigation System," Visteon Corporation, webpage, pp. 1-2 (downloaded Jun. 21, 2002: www.visteon.com/technology/automotive/navmate.html).

"Danger—Products" and "Hiphop Communicator Brochure," Danger, Inc., downloaded Oct. 26, 2003: www.danger.com/products.php).

"MMS phones: Don't believe the hype," CNN.com/SCI-TECH, Aug. 8, 2002, pp. 1-3.

"What is "3G" technology?," CNN.com/SCI-TECH, Oct. 22, 2001, pp. 1-3.

"Devices for Text Messages in Deutsche Telekom's fixed network have already found their way into many households," Deutsche Telekom AG, Press Release, Mar. 13, 2002, pp. 1-2.

"FunMail Launches on the NTT DoCoMo i-mode network," FunMail, Press Release, May 1, 2001, pp. 1-2.

"Send images to i-mode phones," Mobile Media Japan, 2001, pp. 1-3.

"Introduction to SMS," by C. Tull of AnywhereYouGo.com, pp. 1-4 (downloaded: www.devx.com/wireless/articles/SMS/SMSintro-asp).

"The Always on Network," Position Paper, Nortel Networks, 2002.

"Mobile Location Based Services: Cell Tracking Devices of People & Thongs . . . ," pp. 1-2, (downloaded Aug. 10, 2002: http://3glocate.com).

"3G Mobile Internet Revolution, . . . only with Location Based Services!" pp. 1, (downloaded Aug. 10, 2002: http://webhome.idirect.com/~dental/3glocator/home.htm).

"What are Instant Messages?" Yahoo! Messenger Help, Yahoo! Inc., 2002, pp. 1.

"What is a Friend List?" Yahoo! Messenger Help, Yahoo! Inc., 2002, pp. 1.

"Status Icons/Messages," Yahoo! Messenger Help, Yahoo! Inc., 2002, pp. 1-2.

"Yahoo! Messenger for WAP," Yahoo Messenger, Yahoo! Inc., 2002 (tours 1-9), pp. 1-17 (downloaded Oct. 27, 2002: www.messenger.yahoo.com/messenger/wireless/wap/tour1.html (through /tour9.html)).

IMVironment, Yahoo! Meseanger, Yahoo! Inc., 2002, pp. 1-12 (downloaded (including) Oct. 27, 2002: http://help.yahoo.com/help/us/mesg/imv/imv-01.html (through /index5.html).

"Yahoo! Messenger for Text Messaging," Yahoo! Messenger, Yahoo! Inc., 2002, pp. 1-10 (downloaded Oct. 27, 2002: http://messenger.yahoo.com/messenger/wireless/smsmsgr/tour1.html (through /tour7.html)).

"Yahoo! Messenger—Sending Messages to a Mobile Phone," Yahoo! Messenger, Yahoo! Inc., 2002, pp. 1-7 (downloaded Oct. 27, 2002: http://messenger.yahoo.com/messenger/wireless/pc2sms/tourl.html (through /tour7.html)).

LoadTrak, pp. 1-2 (downloaded Jun. 4, 2002: www.load-trak.com).

"pulver.com's Location Based Services Report," pulver.com, Inc., Oct. 2001, pp. 1-17 (downloaded Jun. 4, 2002: www.pulver.com/lbsreport/lastbsreport.02/oct01.txt).

"Wherify Wireless GPS Locator for Kids User Guide," Wherify Wireless, Inc., 2003, pp. 1-106.

"Wherify Wireless and SiRF Team to Deliver Child Locator System," Wherify Wireless, Inc., Press Release, Mar. 19, 2001, pp. 1-2.

"Wherify Wireless Breakthrough in Location-Based Services," Mobilemag.com, Feb. 28, 2001, p. 1.

"Wherify Wireless Location Services," Wherify Wireless, Inc., webpages, pp. 1-5 (downloaded: Mar. 25, 2003: www.wherifywireless.com/prod_watches.htm).

Marek, "The Unstoppable SnapTrack," Wireless Week, Dec. 18, 2000.

Rabinowitz and Spilker, Jr., "Positioning Using the ATSC Digital Television Signal," Rosum Corporation Whitepaper, Rosum Corporation (downloaded May 21, 2003).

Rabinowitz and Spilker, Jr., "A New Positioning System Using Television Synchronization Signals," Rosum Corporation, pp. 1-11 (downloaded May 21, 2003).

"Trimble and Rosum Team to Develop Universal Positioning Technology," Trimble Navigation, Inc., News Release, Feb. 27, 2003.

Wong, "Fishers, golfers join the rush to GPS," San Jose Mercury News, news article, Mar. 25, 2002.

Ryan, "Catching up with Dick Tracy," San Francisco Chronicle, news article, Mar. 18, 2002.

"Theme Park Visitors & Cashless Purchasing," Case Study, RJI Incorporated, webpages, pp. 1-2 (downloaded Mar. 16, 2002: www.rji.cc/casestudies/themepark.html).

"Ski Rental with Auto ID and Tracking," Case Study, RJI Incorporated, webpages, pp. 1-2 (downloaded Mar. 16, 2002: www.rji.cc/casestudies/skirentalcompany.html).

"Real-Time Warehouse Tracking," Case Study, RJI Incorporated, webpages, pp. 1-2 (downloaded Mar. 16, 2002: www.rji.cc/casestudies/rtwarehousetracking.html).

"Frozen Food Warehouse," Case Study, RJI Incorporated, webpages, pp. 1-3 (downloaded Mar. 16, 2002: www.rji.cc/casestudies/frozenfoodwarehouse.html).

"Airline Cargo Containers," Case Study, RJI Incorporated, webpages, pp. 1-2 (downloaded Mar. 16, 2002: www.rji.cc/casestudies/airlinecargocontainers.html).

"Airline Food Carts," Case Study, RJI Incorporated, webpages, pp. 1-2 (downloaded Mar. 16, 2002: www.rji.cc/casestudies/airlinefoodcarts.html).

"Real Time Location System (RTLS)," Case Study, RJI Incorporated, webpage, p. 1 (downloaded Mar. 16, 2002: www.rji.cc/technology/rtls.html).

"Radio Frequency Identification (RFID)," Case Study, RJI Incorporated, webpage, p. 1 (downloaded Mar. 16, 2002: www.rji.cc/technology/rfid.html).

"MoniTrack," Case Study, RJI Incorporated, webpages, pp. 1-2 (downloaded Mar. 16, 2002: www.rji.cc/technology/telematic.html).

"Parkwatch and Wherenet Unveil the First Amusement Visitor Locating System," ParkWatch, Press Release, Jun. 27, 2000.

"Locate Networks: Our Service," Locate Networks, webpages, pp. 1-7 (downloaded Sep. 26, 2002: www.locatenetworks.com/).

"Technical Applications of Our Current Technology," Aetherwire, webpages, pp. 1-4 (downloaded Mar. 16, 2002: www.aetherwire.com/CDROM/General/appl1.html).

Bickers, "Eyes in the sky," SafeTzone Technology Corporation, webpages, 2001, pp. 1-3 (downloaded: www.safetzone.com/newsKiosk.asp).

"IO Data Develops GPS Adapter for I-Mode Mobile," AsiaBizTech, Sep. 17, 2002, pp. 1-2.

"Pakhound: Your Watchdog In The Shipping Industry," website pages, pp. 1-3 (downloaded Jun. 9, 2002: www.pakhound.com/fact.asp).

"Guide to Tracking Info.," Nippon Express, website page, p. 1 (downloaded Jun. 9, 2002: www.nittsu.co.jp/edoc/howtoe.htm).

My.Roadway!, Roadway Express, Inc., webpages, pp. 1-2, (downloaded Jun. 9, 2002: www.quiktrak.roadway.com/cgi-bin/quiktrak).

Packtrack™, PackTrack.com, webpages, pp. 1-2 (downloaded Jun. 9, 2002: www.packtrack.com).

"Welcome to Traker Systems," Tracker Systems, webpages, pp. 1-2 (downloaded Jun. 9, 2002: www.trakersystems.com).

"Welcome to Iship, Inc.," iShip, Inc., webpages, pp. 1-2, (downloaded Jun. 9, 2002: www.iship.com/).

"Turning Position Into Knowledge," SkyBitz, webpage, p. 1, (downloaded Nov. 15, 2002: www.skybitz.com).

"News," SkyBitz, webpages, pp. 1-8, (downloaded Nov. 15, 2002: www.skybitz.com/about/news.html).

"GLS Communicator," SkyBitz, webpages, pp. 1-2, (downloaded Nov. 15, 2002: www.skybitz.com/gls/communicator.html).

"Global Locating Services," SkyBitz, webpage, p. 1, (downloaded Nov. 15, 2002: www.skybitz.com/services/gls.html).

F. Rivera, "Special Report: Keeping Tabs on Your Teen," 7 News, Boston, Apr. 30, 2002, pp. 1-3.

GPS2000, Omega Research and Development, Inc., webpages, pp. 1-9 (pp. 7-9 pertain to an online tour) (downloaded Jul. 14, 2003: www.gps2000online.com/).

"Track Your FedEx Shipments via Email," FedEx, webpages, pp. 1-2 (downloaded Oct. 29, 2002: www.fedex.com).

"Track Shipments—Detailed Results," FedEx, webpages, pp. 1-2 (downloaded Oct. 29, 2002: www.fedex.com).

FedEx Insight, FedEx, webpages, pp. 1-11 (downloaded Oct. 29, 2002: www.fedex.com).

"Tracking Helpful Tips," United Parcel Service of America, Inc. (UPS), webpages, pp. 1-2 (downloaded Jun. 1, 2002: www.ups.com/tracking/nm_help.html).

"MY UPS.COM Benefits," United Parcel Service of America, Inc. (UPS), webpage, p. 1 (downloaded Apr. 13, 2002: www.ups.com/myupsinfo/info/benefits?pnav=stdsservice).

"Enhanced Tracking," United Parcel Service of America, Inc. (UPS), webpages, pp. 1-2 (downloaded Jun. 1, 2002: www.ups.com/myupsinfo/info/etrack?pnav=stdservice).

"UPS Package Tracking," United Parcel Service of America, Inc. (UPS), webpages, pp. 1-2 (downloaded Apr. 13, 2002: www.ups.com/tracking/tracking.html).

"UPS Wireless Solutions," United Parcel Service of America, Inc. (UPS), webpage, p. 1 (downloaded Apr. 13, 2002: www.ups.com/myupsinfo/info/wireless?pnav=stdsservice).

Crossbow Product Guide—Accelerometers, Crossbow Technology, Inc., webpages, pp. 1-3 (downloaded Apr. 11, 2002: www.xbow.com/Products/Accelerometers.htm).

Accelerometers—General Purpose, LP Series, Crossbow Technology, Inc., data sheet, pp. 1-3 (downloaded Apr. 11, 2002: www.xbow.com/Products/Accelerometers.htm).

Precision Accelerometers, PCB Piezoelectronics Products—SVS Division, webpages, pp. 1-2 (downloaded Apr. 11, 2002: www.pcb.com/products/svs/index.html).

"352C22 Miniature Low Profile ICP Accelerometer," Precision Accelerometers, PCB Piezoelectronics Products—SVS Division, webpages, pp. 1-2 (downloaded Apr. 11, 2002: www.pcb.com/products/svs/svs352c22.html).

K. Hill, "Prada Uses Smart Tags To Personalize Shopping," CRMDaily.com, Apr. 24, 2002., pp. 1-4.

"Savi Reusable Transport Container," Savi Technology, Inc., Apr. 30, 2002, pp. 1-2.

"Developing a GPSs for the Global Supply Chain," Aberdeen Group, Inc., Executive White Paper, Jun. 2002.

Motorola Consumer Catalog: Pagers (webpage), Motorola, Inc., downloaded Jan. 19, 2000.

SnapTrack in Action (webpage), SnapTrack Inc., downloaded Jan. 19, 2000.

SnapTrack—Technology At Work (webpage), SnapTrack Inc., downloaded Jan. 19, 2000.

SnapTrack—Privacy Protection (webpage), SnapTrack Inc., downloaded Jan. 19, 2000.

"An Introduction to SnapTrack Server-Aided GPS Technology," SnapTrack Inc.

"SnapTrack and SignalSoft Corp. Team Up to Trial Location-based Information Service for GSM Test Group," Press Release, SnapTrack Inc., Dec. 6, 1999.

"SnapTrack Awarded Additional Key Patents for Enhanced GPS System," Press Release, SnapTrack Inc., Jan. 4, 2000.

Commercial Uses for LoJack (webpage), LoJack Corporation, downloaded Jan. 22, 2000.

Chertkoff, Rachel, "Vehicle Locator Systems," Pager Technology, pp. 1-2, 1998.

"EarthTrack™ Vehicle Tracking Systems," Outfitter Satellite, Inc., 1998 (downloaded Jan. 22, 2000).

Kleinknecht, William, "Juvenile authorities want satellite tracking for felons," The Star-Ledger of New Jersey, Nov. 18, 1997.

* cited by examiner

LOCATION RECORD

| CURRENT | LABEL | LONG. | LAT. | TIME | DATA |
|---|---|---|---|---|---|
| 0 | Home | X1 | Y1 | 5:45 pm | 1/1/02 |
| 1 | 7 Eleven | X2 | Y2 | 5:30 pm | 1/1/02 |
| 2 | RT. 101 | X3 | Y3 | 5:15 pm | 1/1/02 |
| 3 | Work | X4 | Y4 | 5:00 pm | 1/1/02 |

HEALTH RECORD

| CURRENT | BP | HB | TEMP. | BR | DURATION |
|---|---|---|---|---|---|
| 0 | 160/85 | 70 | 98 | 15 | - |
| 1 | 180/80 | 100 | 99 | 30 | .3 |
| 2 | 160/85 | 75 | 98 | 15 | 1.1 |
| 3 | 150/90 | 60 | 98 | 10 | 8 |

ACTION RECORD

520

| NOTIFY | Y |
|---|---|
| ALERT | Y |
| GUIDANCE | N |
| 911 | Y |

FIG. 5C

NOTIFY RECORD

530

| ACTIVITY | BP | HB | TEMP. | BR |
|---|---|---|---|---|
| General | 170-199 / 70-99 | >180 <120 | 101-104 | >50 |
| Exercising | 170-199 / 70-99 | >180 <20 | 102-104 | >60 |
| Sleeping | 170-199 / 70-99 | >180 <20 | 101-104 | >50 |

FIG. 5D

ALERT RECORD ⟵ 540

| ACTIVITY | BP | HB | TEMP. | BR |
|---|---|---|---|---|
| General | 180-199 / 80-99 | 110 - 120 | 103 - 104 | >50 |
| Exercising | 180-199 / 80-99 | 180 - 200 | 103 - 104 | >60 |

FIG. 5E

GUIDANCE RECORD ⟵ 550

| ACTIVITY | BP | HB | TEMP. | BR | MSG. |
|---|---|---|---|---|---|
| General | 180-199 / 80-99 | 110 - 120 | 103 - 104 | >60 | #1 |
| Exercising | 180-199 / 80-99 | 180 - 200 | 103 - 104 | >60 | #2 |

FIG. 5F

911 RECORD

| BP | HB | TEMP. |
|---|---|---|
| >200 / >100 | >200<br><10 | >105 |

METHOD AND SYSTEM FOR PERSONALIZED MEDICAL MONITORING AND NOTIFICATIONS THEREFOR

CROSS REFERENCE TO RELATED APPLICATIONS

This application claims benefit of: (i) U.S. Provisional Patent Application No. 60/444,198, filed Jan. 30, 2003, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

This application is also related to: (i) U.S. patent application Ser. No. 10/397,473, filed Mar. 26, 2003, now U.S. Pat. No. 6,975,941, and entitled "METHOD AND APPARATUS FOR INTELLIGENT ACQUISITION OF POSITION INFORMATION;" (ii) U.S. patent application Ser. No. 10/397,472, filed Mar. 26, 2003, now U.S. Pat. No. 7,218,938, and entitled "METHODS AND APPARATUS TO ANALYZE AND PRESENT LOCATION INFORMATION;" (iii) U.S. patent application Ser. No. 10/397,637, filed Mar. 26, 2003, now U.S. Pat. No. 7,212,829, and entitled "METHOD AND SYSTEM FOR PROVIDING SHIPMENT TRACKING AND NOTIFICATIONS:" (iv) U.S. patent application Ser. No. 10/397,640, filed Mar. 26, 2003, and entitled "INEXPENSIVE POSITION SENSING DEVICE;" (v) U.S. patent application Ser. No. 10/397,474, filed Mar. 26, 2003, and entitled "METHOD AND SYSTEM FOR ENHANCED MESSAGING;" and (vi) U.S. patent application Ser. No. 10/397,512, filed Mar. 26, 2003, and entitled "APPLICATIONS OF STATUS INFORMATION FOR INVENTORY MANAGEMENT."

BACKGROUND OF THE INVENTION

1. Field of the Invention

The present invention relates to medical condition monitoring and, more particularly, to remote monitoring of medical conditions and locations of persons.

2. Description of the Related Art

Medical conditions are often monitored for patients while admitted at a hospital or while at a doctor's office. The monitoring can assist a doctor or other medical professional in diagnosis or treatment of a patient. Typically, a specialized monitoring machine would be placed nearby the patient and then one or more sensors would be affixed to the patient. Periodically, a doctor or other medical professional would view the data output by the specialized monitoring machine. Some medical monitoring devices are portable. These portable devices permit the patient's health to be monitored over an extended period of time. A doctor or other medical professional would view the data gathered at the next visit of the patient to a hospital or doctor's office. However, typically, these medical devices, whether stationary or portable, are special purpose devices that require professionals or trained technicians to setup and use. It is unfortunate that the use of such medical devices to monitor patients outside of a hospital or doctor's office requires professional assistance and expensive equipment. These disadvantages make it impractical for widespread use of medical monitoring systems.

Thus, there is a need for improved methods and systems to facilitate personal medical monitoring.

SUMMARY OF THE INVENTION

Broadly speaking, the invention relates to improved methods and systems for personal medical monitoring. The monitoring yields status information pertaining to persons being monitored. Notifications, recommendations and/or actions can be initiated by examination or analysis of the status information.

One aspect of the invention pertains to methods and systems for monitoring status information, including health conditions, of persons. Another aspect of the invention pertains to methods and systems for providing notifications to one or more persons. The notifications can contain status information pertaining to the person being monitored. Still another aspect of the invention pertains to methods and systems for inducing an action for or on a person based on the status information of the person. Yet still another aspect of the invention pertains to methods and systems that use a web server for remote access to monitor the status of persons being monitored and/or for facilitating configuration of notifications, recommendations and/or actions to be provided. Hence, interested parties can gain access to status information pertaining to the persons being monitored via a website or, more generally, a data network (e.g., the Internet).

According to one embodiment, the status information can include health, position (location) and other information. One example of other information is environmental conditions.

The invention can be implemented in numerous ways including, a method, system, device, graphical user interface, and a computer readable medium. Several embodiments of the invention are discussed below.

As a health monitoring system, one embodiment of the invention includes at least: a plurality of medical monitoring devices affixed to persons to be monitored, the medical monitoring devices producing location information and health condition information; and a monitoring server operatively connected to the medical monitoring devices via a first network, the monitoring server receiving and storing the location information and the health condition information from the medical monitoring devices. The first network includes at least a wired network and a wireless network.

As a method for monitoring status of a person, one embodiment of the invention includes at least the acts of: acquiring status information of the person being monitored, the status information including at least health information of the person; obtaining threshold conditions to be applied; determining whether an action condition exists by comparing the health information with the threshold conditions; and initiating an action when the determining determines that the action condition exists.

As a method for monitoring status of a person, another embodiment of the invention includes at least the acts of: receiving status information of a person being monitored, the status information being provided by a status-aware mobile device affixed to the person, the status information including at least a location of the status-aware mobile device affixed to the person and a health condition of the person; determining whether a notification should be provided to the person based on at least the health condition of the person; generating a notification message based on the location and the health condition when the determining determines that a notification should be provided; and providing the notification message to the person.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which:

FIGS. 5A-5G are exemplary records of a database according to one embodiment of the invention.

DETAILED DESCRIPTION OF THE INVENTION

Figure 1:
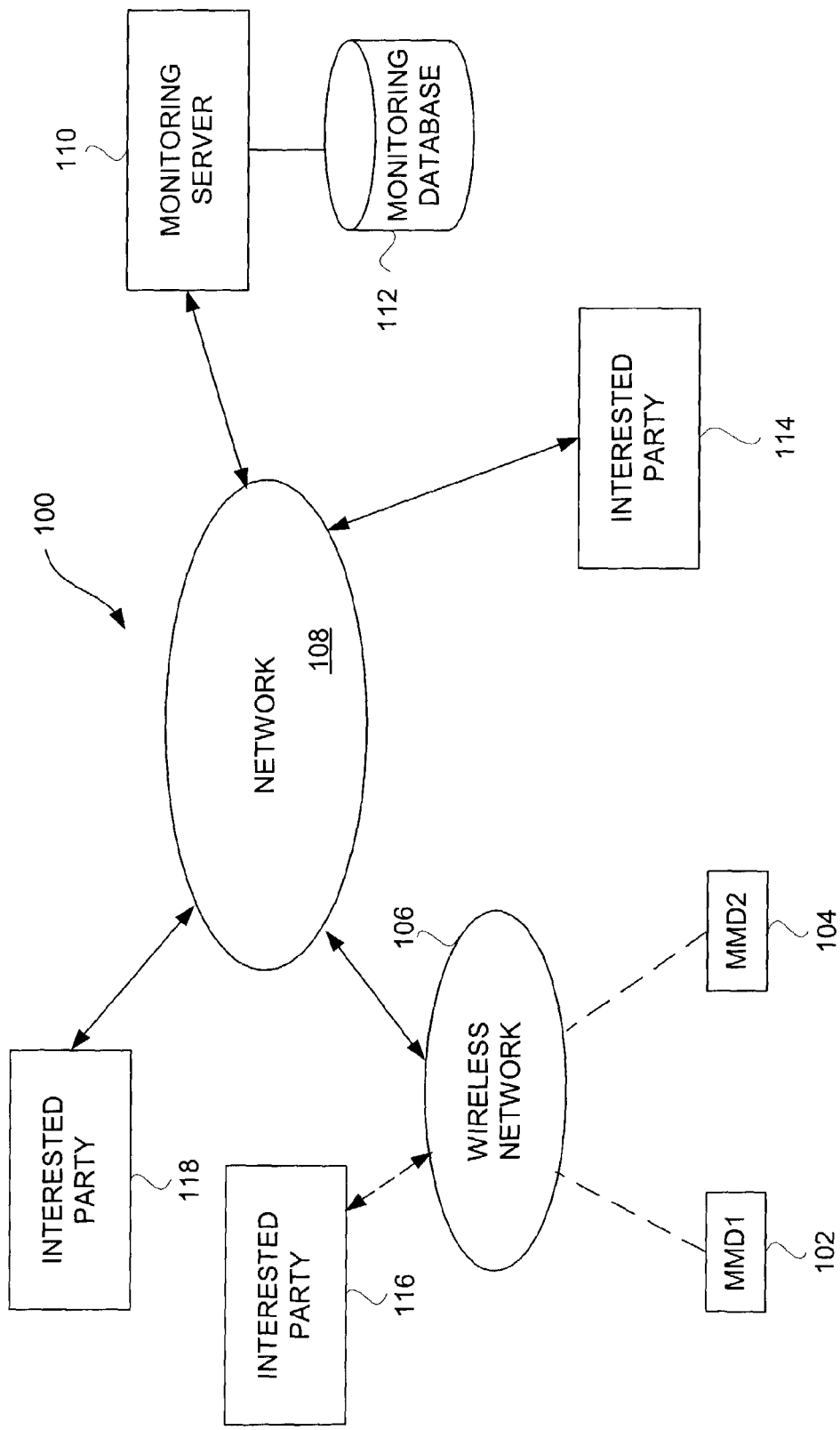
FIG. 1 is a health monitoring system according to one embodiment of the invention.

The invention relates to improved methods and systems for personal medical monitoring. The monitoring yields status information pertaining to persons being monitored. Notifications, recommendations and/or actions can be initiated by examination or analysis of the status information.

One aspect of the invention pertains to methods and systems for monitoring status information, including health conditions, of persons. Another aspect of the invention pertains to methods and systems for providing notifications to one or more persons. The notifications can contain status information pertaining to the person being monitored. Still another aspect of the invention pertains to methods and systems for inducing an action for or on a person based on the status information of the person. Yet still another aspect of the invention pertains to methods and systems that use a web server for remote access to monitor the status of persons being monitored and/or for facilitating configuration of notifications, recommendations and/or actions to be provided. Hence, interested parties can gain access to status information pertaining to the persons being monitored via a website or, more generally, a data network (e.g., the Internet).

According to one embodiment, the status information can include health, position (location) and other information. One example of other information is environmental conditions.

In the following description, numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Embodiments of the invention are discussed below with reference to FIGS. 1-11. However, those skilled in the art will readily appreciate that the detailed description given herein with respect to these figures is for explanatory purposes as the invention extends beyond these limited embodiments.

FIG. 1 is a health monitoring system 100 according to one embodiment of the invention. The health monitoring system 100 operates to monitor health conditions or status of one or more persons. Each person having their status (e.g., health) monitored by the health monitoring system 100 has affixed thereto a medical monitoring device (MMD) 102. The medical monitoring devices 102 can be affixed to the person in a variety of ways, such as carried by the person (including carried by the person's clothing), worn by the person, located under the skin or internal to the person (i.e., in vitro or invasive to the person), etc. Examples of ways to wear such a medical monitoring device include inside a pocket of a clothing the person wears or right on the person (e.g., a piece of jewelry, watch or patch worn by the person). The medical monitoring devices 102 and 104 are described in more detail below but generally include medical sensors and communication capabilities. The medical monitoring devices 102 and 104 are coupled to a wireless network 106. In one embodiment, the wireless network 106 is a data network. For example, the data network can be a Short Message Service (SMS) network, a cellular network, a local wireless network (Bluetooth, Wi-Fi, etc.) or other wireless network. The wireless network 106 also couples to a network 108. In one embodiment, the network 108 includes at least a portion of the Internet (i.e., a global computer network). In another embodiment, the network 108 is a local area network or a wide area network. In general, the network 108 can be a wired network, a wireless network or both.

A monitoring server 110 can couple to the network 108. The monitoring server 110 can store status information (e.g., medical conditions) associated with the various persons having their status (e.g., health) being monitored by the medical monitoring devices 102 and 104. Typically, the monitoring server 110 would couple to a monitoring database 112 that stores the status information pertaining to the various users (persons). In this regard, the medical monitoring devices 102 and 104 communicate through the wireless network 106 over wireless links and can then communicate through the wireless network 106 with the monitoring server 110 via the network 108.

Additionally, an interested party 114 may also wish to interact or communicate with the medical monitoring devices 102 and 104 or the monitoring server 110. The interested party 114 is shown as being coupled to the network 108. Alternatively, an interested party 116 can also couple directly to the wireless network 106 such that the interested party 116 is able to communicate in a wireless manner either with the medical monitoring devices 102 and 104 or with the monitoring server 110 via the wireless network 106 (or some other wireless network) that couples to the network 108. Still further, an interested party 118 may also be interested in monitoring or receiving the status information pertaining to the persons having their status monitored. In one embodiment, any of the interested party 114, the interested party 116 and/or the interested party 118 can interact with the monitoring server 110 to access the status information pertaining to the persons having their status (e.g., health) monitored. In another embodiment, any of the interested party 114, the interested party 116 or the interested party 118 can interact with the monitoring server 110 to configure type, frequency and/or conditions that are to cause actions (e.g., notifications) to the interested party.

The health monitoring system 100 shown is FIG. 1 is a representative embodiment. Other embodiments of health monitoring systems can also support many medical monitoring devices, zero or more third-parties, zero or more interested parties, and zero or more monitoring servers. Also, in general, health monitoring systems can by peer-to-peer or centralized, or both. Peer-to-peer can involve status information being transmitted between medical monitoring devices, whereas centralized can involve status information being provided to a central server (e.g., monitoring server 110) and then accessible obtained from the central server.

Figure 2:
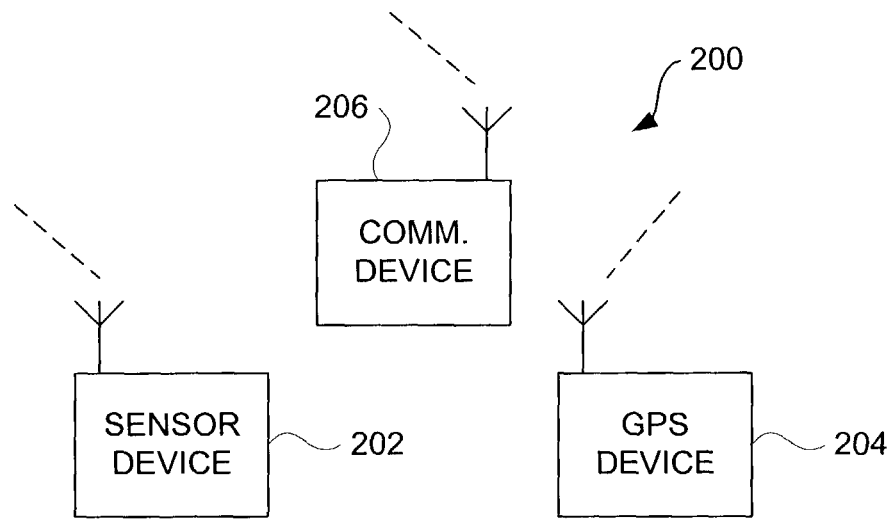
FIG. 2 is a block diagram of a medical monitoring device according to one embodiment of the invention.
Figure 3:
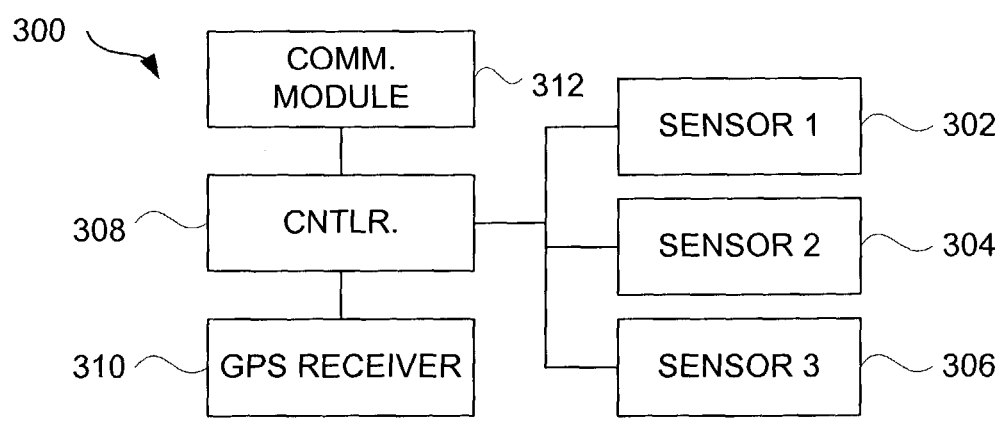
FIG. 3 is a block diagram of a medical monitoring device according to another embodiment of the invention.

Medical monitoring devices detect status information pertaining to persons, which can include health conditions. FIGS. 2 and 3 are embodiments of two representative medical monitoring devices. Additional details on medical monitoring devices can be found in U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference.

FIG. 2 is a block diagram of a medical monitoring device 200 according to one embodiment of the invention. The medical monitoring device 200 is, for example, suitable for use as the medical monitoring device 102 or 104 illustrated in FIG. 1. The medical monitoring device 200 includes a sensor device 202, a GPS device 204, and a communication device 206. The medical monitoring device 200 is designed such that the sensor device 202 and the GPS device 204 are able to communicate with the communication device 206 in a wireless manner. The communication device 206 is then able to communicate with a wireless network (e.g., the wireless network 106) in a wireless manner. In one embodiment, the medical monitoring device 200 is worn by a person. One or more of the sensor device 202, the GPS device 204 and the communication device 206 can be provided separately. Separate devices permit flexible positioning of the devices on the person and also permit devices to be interchangeable. In one embodiment, the separate devices are each wearable by the person and communicate with one another in a wireless manner.

FIG. 3 is a block diagram of a medical monitoring device 300 according to another embodiment of the invention. The medical monitoring device 300 has an integrated design that is typically implemented as a single package. The medical monitoring device 300 can include a plurality of sensors 302, 304 and 306 that couple to a controller 308. The controller 308 can process the sensor data to the extent desired. In addition, a GPS receiver 310 can receive location data from GPS satellites and provide such location data to the controller 308. The controller 308 further controls the information about the sensor data and the location data that is communicated to the person, an interested party, or a monitoring server. When communication over a wireless link is needed, the controller 308 interacts with a communication module 312 to achieve the appropriate wireless communication.

The components can also be combined or integrated on a common integrated circuit chip to permit or facilitate sharing of some circuitry with other components or devices. For example, circuitry can be shared amongst the GPS receiver 310 and the communication module 312. As another example, circuitry can be shared amongst the sensors 302, 304 and 306. In any case, the sensors 302, 304 and 306 may couple to the person being monitored. In one embodiment, the medical monitoring device 300 is small and lightweight and thus easily wearable.

In one example, a medical monitoring device can be a mobile telephone having communication circuitry, a GPS receiver and one or more medical sensors. The sensors can be internal or external to the mobile telephone. In the case of external sensors, the sensors can couple to the mobile telephone through a wire or cable or through wireless means (e.g., Bluetooth or Wi-Fi).

Figure 4:
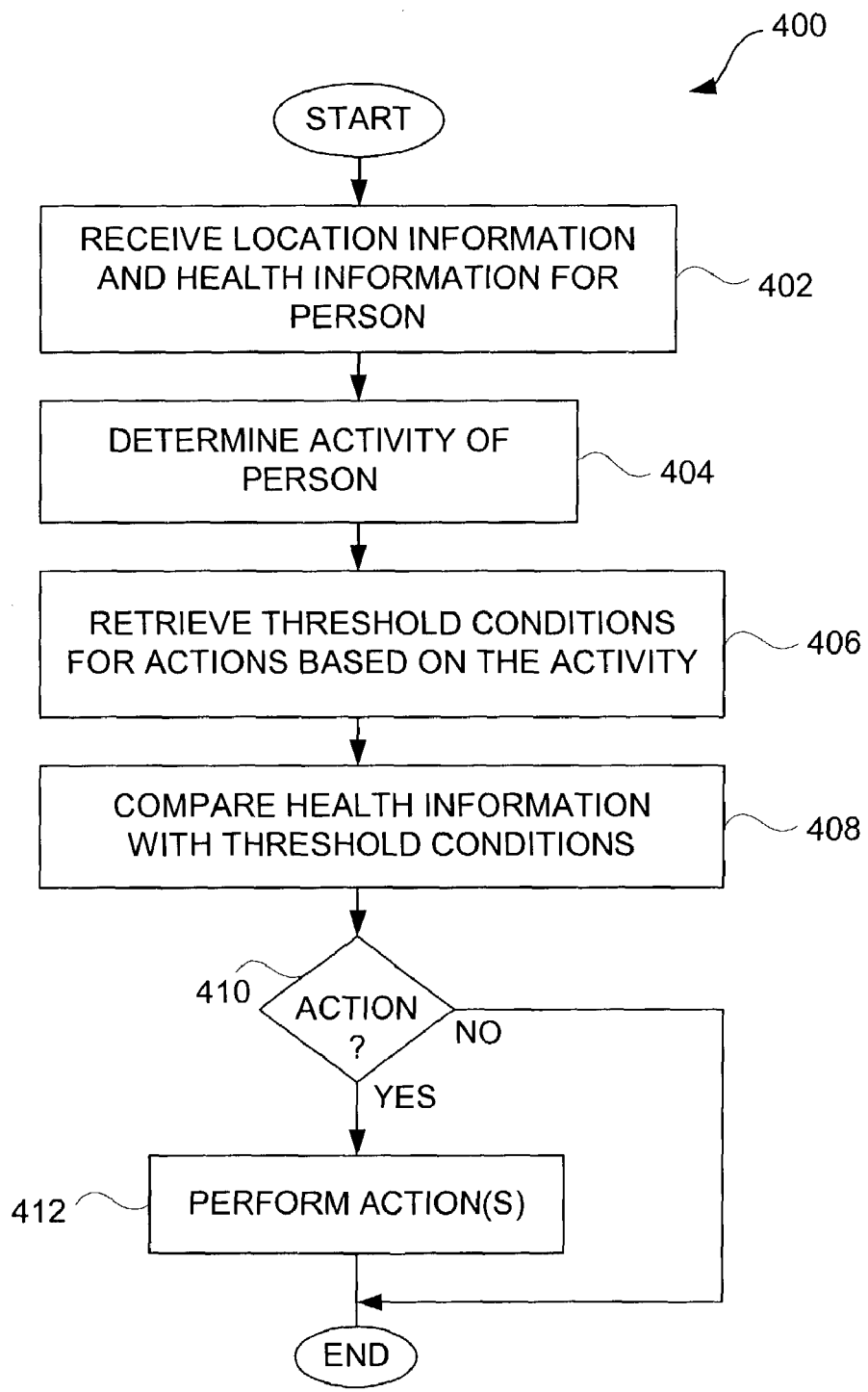
FIG. 4 is a flow diagram of an automated health processing according to one embodiment of the invention.

FIG. 4 is a flow diagram of automated health processing 400 according to one embodiment of the invention. The automated health processing 400 initially receives 402 location information and health information (medical conditions) for a person. The location information and the health information for the person are provided by a medical monitoring device. The medical monitoring device can also obtain other sensor data, such as temperature, velocity, acceleration, etc. The health information, the location information and the other sensor data can be generally considered status information.

Next, an activity of the person is determined 404. In one implementation, the activity of the person can be determined 404 based on location information and/or the other sensor data. For example, in one example, the activity of the person is distinguished between sleeping, walking, running, driving, etc. based upon velocity of movement of the person determined from a plurality of location information and/or particular sensor data. Next, threshold conditions for actions are retrieved 406 based on the activity. Note that the threshold conditions for actions can differ depending upon the activity of the person. For example, if the person is exercising, then it is expected that there should be different threshold conditions with respect to certain medical conditions, as compared to threshold conditions for use when the person is sleeping. Next, the health information is compared 408 with the threshold conditions.

A decision 410 then determines whether an action should be performed based on the result of the comparison 408. When the decision 410 determines that an action should be performed, then one or more actions are initiated 412.

The actions that can be performed 412 can vary with application. In one embodiment, the actions can include a notification or a treatment. A notification can be a message or an alert. The notifications can use any combination of text, image, audio, video or tactile action to present the notification to a user (e.g., person or interested party). In one embodiment, the notification can provide the user with information about location information and/or health information of the person. In another embodiment, the notification can provide instructions or guidance for the user. For example, the instructions or guidance can direct the person to a hospital or pharmacy and optionally also provide navigation directions. As another example, the instructions or guidance can recommend the user do certain thing to help his health condition, such as rest, take certain medicine, visit doctor, etc.

A treatment can be automatically performed on the person. In one embodiment, the medical monitoring device controls a treatment induced on the person. As examples, the treatment can automatically cause an injection of a substance to the person, release of a chemical (e.g., medicine) to the person, etc. In one embodiment, the notification and/or treatment can be dependent on one or more of the person's health conditions, the person's location, the person's activity, or the person's previous status information (e.g., health history).

Alternatively, when the decision 410 determines that no action is to be performed, then the operation 412 is bypassed. After the operation 412, or its being bypassed, the automatic health monitoring 400 is complete and ends.

The health and location information acquired by a medical monitoring device can be stored to a database, such as the monitoring database 112 illustrated in FIG. 1. Alternatively, the database could reside within a medical monitoring device or be provided elsewhere within the health monitoring system 100.

Figure 5A:

In one embodiment, each person being monitored by a medical monitoring device would have a User Identifier (UI), which can be known as a Global User Identifier (GUID). In one embodiment, the GUID can be used to link together various records within the database. For example, according to one embodiment, the records associated with a person that are stored in a database can include a location record 500 illustrated in FIG. 5A, a health record 510 illustrated in FIG. 5B, an action record 520 as illustrated in FIG. 5C, a notify record 530 as shown in FIG. 5D, an alert record 540 as shown in FIG. 5E, a guidance record 550 as shown in FIG. 5F, and a 911 record 560 as shown in FIG. 5G. The data presented in these records is merely for illustrative purposes.

The location record 500 shown in FIG. 5A can include a history of location information for the person. The location information can include a label for the location, as well as longitude and latitude data (i.e., position data) therefore. The location record 500 can also indicate time and date when the person was at the corresponding locations.

Figure 5B:
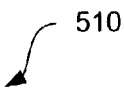
Figure 5G:

The health record 510 shown in FIG. 5B can include a history of health information, such as blood pressure (BP), heart beat (HB), and temperature (Temp.), and breathing rate per minute (BR). The health record 510 may also include duration information indicating an approximate duration (e.g., in seconds) during which the health conditions were essentially the same.

The action record 520 shown in FIG. 5C indicates the types of actions that are to be enabled. The enabled actions can then be triggered based on the health and location information retrieved from a medical monitoring device and the corresponding threshold conditions. For example, in one embodiment, the actions available for initiation or performance by a health monitoring system might include a notification, an alert, guidance or a 911 emergency call. A user, such as a system administrator or interested party, would be able to select or configure the actions to be performed for a given person being monitored.

When a notify action is to be performed, the database can include the notify record 530. The notify record 530 shown in FIG. 5D is a representative notification record which can contain threshold conditions for medical conditions to trigger notifications. Further, as shown in FIG. 5D, different sets of threshold conditions can be provided dependent upon the type of activity (e.g., general, exercising, sleeping) performed, or determined (estimated) to be performed, by the person being monitored. Typically, the notifications are to one or more interested parties. One example of a notification is an electronic mail message that contains medical condition information pertaining to the person being monitored.

The alert record 540 shown in FIG. 5E determines the threshold conditions associated with providing an alert to the person having their health and location being monitored. The alert record 540 shown in FIG. 5E is a representative alert record which can contain threshold medical conditions to trigger alerts. Different sets of threshold conditions can be provided dependent upon the type of activity performed or determined (estimated) to be performed by the person being monitored.

The guidance record 550 shown in FIG. 5F provides threshold medical conditions associated with triggering a guidance action. The guidance thresholds may be the same as the alert thresholds shown in FIG. 5E. However, the actions can be quite different. For example, an alert action can be a series of loud beeps. However, a guidance action is typically more involved. A guidance action can involve presenting one or more recommendations. The guidance action can be presented to the person by audio, graphical and/or textual means. Since the location of the person is known, the guidance can be guiding the person to a nearby pharmacy to buy a certain medicine, or to a nearby hospital to have a certain medical examination performed. Again, different threshold conditions can be provided for different activities that the person being monitored is undergoing, or for different prior medical conditions of the person.

In FIG. 5G, the 911 record 560 indicates the emergency threshold conditions for medical conditions that are used to trigger an automated 911 call. The 911 call can be an automated telephone call to a hospital, emergency response unit, (e.g., ambulance), health care provider, doctor, close relative and the like.

To trigger an action, at least one of the multiple threshold values provided in the records shown in FIGS. 5D-5G, would normally have been exceeded. In general, one or more of the thresholds can be required to be exceeded before the corresponding action is triggered.

In yet another embodiment, different threshold conditions can be set or customized based on a piece of demographic information related to the person, such as the person's ethnicity, age, gender or lifestyle. The demographic information can also include where the person resides or is presently located. For example, if the person resides or is presently located in the middle of the Sahara Desert or in the North Pole, one or more of the threshold conditions can be different.

In still another embodiment, threshold conditions can also depend on the person's prior medical conditions. More generally, different people can have same or different threshold conditions.

Although not discussed with respect to FIGS. 5A-5G, an action can include a treatment. In one embodiment, there is an additional record in the database related to the treatment performed on the person. The record can include the time, the type, and the amount of treatment administered to the person.

Still further, the database can include various other records. For example, the database could include a record that stores the status of a person when an action is initiated. As another example, a record could store the status of a person during a treatment. Still another record could archive the status of the person and actions taken.

Figure 6:
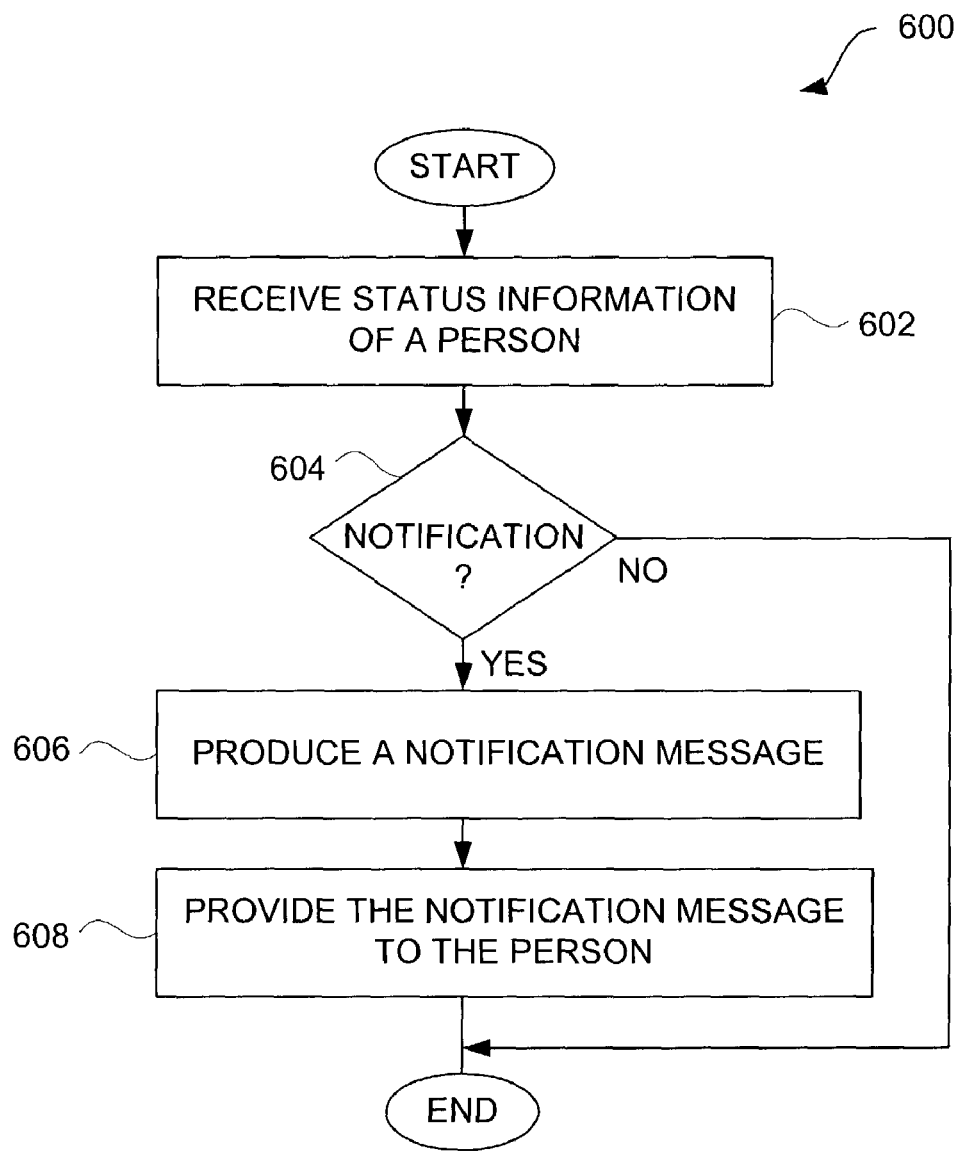
FIG. 6 is a flow diagram of personal notification processing according to one embodiment of the invention.

FIG. 6 is a flow diagram of personal notification processing 600 according to one embodiment of the invention. The personal notification processing 600 can, for example, be performed by a medical monitoring device (e.g., medical monitoring device 200, 300).

The personal notification processing 600 receives 602 status information of a person. The status information of the person can be provided by the medical monitoring device affixed to the person. A decision 604 then determines whether a notification is to be performed. The decision 604 involves an analysis of the status information of the person. Typically, the status information includes health information and location information pertaining to the person (or the medical monitoring device affixed to the person). The status information might also include environmental conditions (e.g., ambient temperature, humidity, etc.) associated with the location of the person (or the medical monitoring device). Hence, the analysis being performed determines whether the person should be notified based on the status information. In one embodiment, the health and/or location information of the status information are compared with notification criteria (e.g., threshold values). The notification criteria can, for example, be general purpose or user-specific.

The notification criteria can be set or determined in a variety of different ways. For example, the notification criteria can be dynamically determined, user-provided, or third-party provided. Typically, the determination of whether a person should be notified is based on the status information and the notification criteria. In one embodiment, the notification criteria is particular to the person being monitored. In other words, the notification criteria can be different for different persons. In another embodiment, the notification criteria can additionally or alternatively depend upon the location or activity being performed by the person.

When the decision 604 determines that no notification is to be provided, then the personal notification processing 600 is complete and ends with no notification having been performed. On the other hand, when the decision 604 determines that a notification is desired, then a notification message is produced 606.

The notification message can take a variety of different forms but generally serves to notify the person of their medical condition and/or steps to take given their medical condition. For example, the notification message can be a text message that is displayed on a small display of the medical monitoring device, a voice message that is played by the medical monitoring device, or an audio sound that is played by the medical monitoring device. After the notification message has been produced 606, the notification message is provided 608 to the person. Depending upon the type of notification message, the notification message could be provided in a different manner. For example, a text message could be provided to the person by displaying the notification message of a display of the medical monitoring device. Since the display is typically small, multiple screens or scrolling may be used to display the notification message. A voice message type notification would be provided to the person by the medical monitoring device playing the voice message. Following the operation 608, the personal notification processing 600 is complete and ends with one or more notification messages having been provided to the person. Nevertheless, the personal notification processing 600 can continue periodically, on-demand or as the status information is updated.

Figure 7:
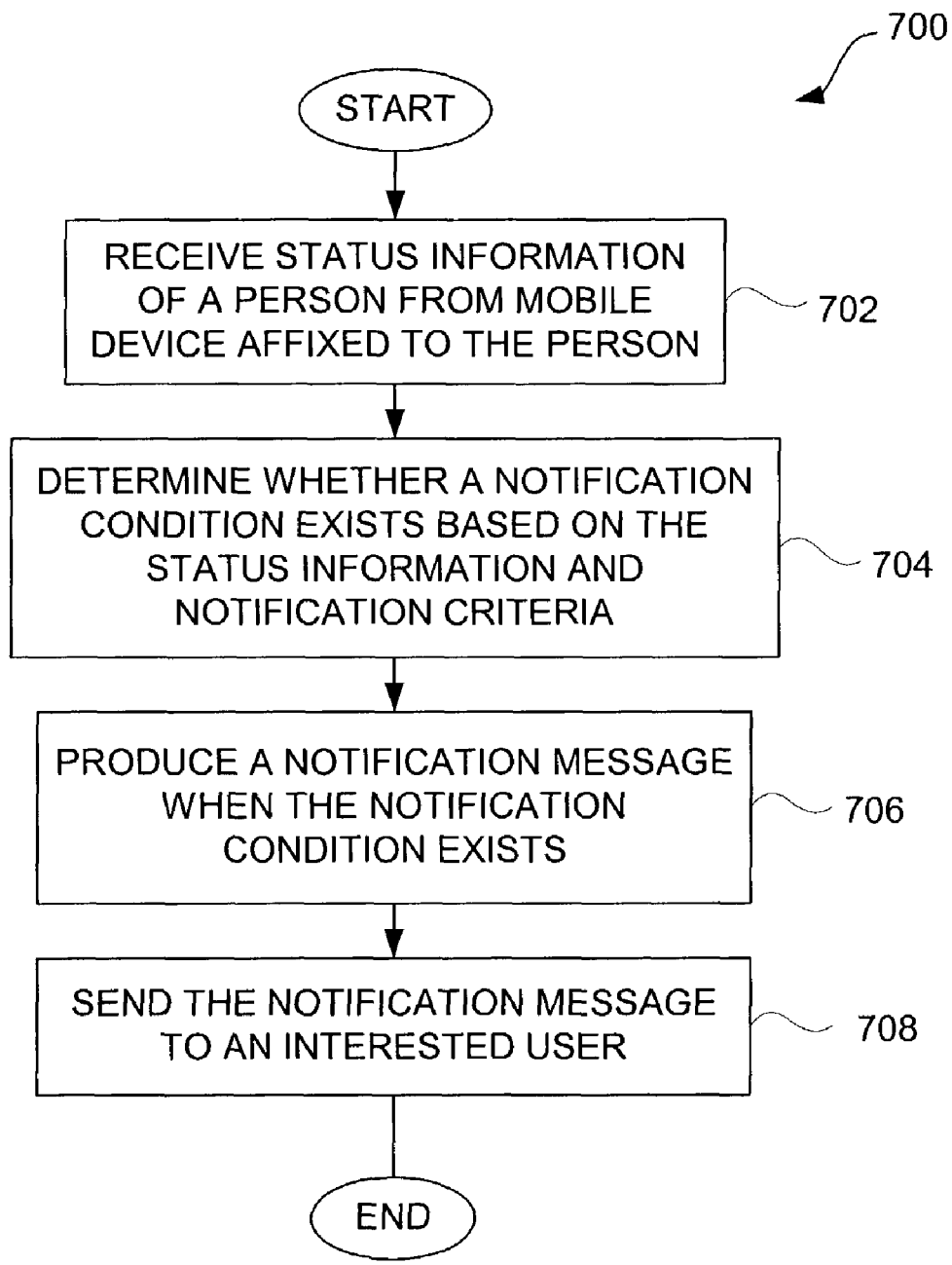
FIG. 7 is a flow diagram of remote notification processing according to one embodiment of the invention.

FIG. 7 is a flow diagram of remote notification processing 700 according to one embodiment of the invention. The remote notification processing 700 serves to notify remotely-located interested users of the health condition of a person being monitored. The remote notification processing 700 is, for example, performed by a medical monitoring device alone or with assistance with a monitoring server.

The remote notification processing 700 receives 702 status information of a person. The status information is provided by a mobile device (e.g., medical monitoring device) that is affixed to the person. Then, the remote notification processing 700 determines 704 whether a notification condition exists based on the status information and notification criteria. The notification criteria can be set or determined in a variety of different ways. For example, the notification criteria can be dynamically determined, user-provided, or third-party provided. In any case, the determination of whether a notification condition exists typically is based on the status information and the notification criteria. In one embodiment, the notification criteria are particular to the person being monitored. In other words, the notification criteria can be different for different persons. In another embodiment, the notification criteria can additionally or alternatively depend upon the location or activity being performed by the person.

Thereafter, assuming a notification condition does exist, a notification message is produced 706. As noted above, the notification message can be of a variety of different types, including text, voice and audio. After the notification message has been produced 706, the notification message is sent 708 to an interested user. An interested user can be anyone desirous of receiving notification messages pertaining to the status of the person being monitored. Here, the notification message is sent to a wireless and/or wired network to a device associated with the interested user. For example, when the notification message is an electronic mail message, the electronic mail message can be transmitted through a wired or wireless network to a communication or computing device associated with the interested user. The interested user is then able to receive and read the electronic mail message and thus being informed of the health condition of the person being monitored. Similarly, the notification message might be a voice message that is transmitted to the interested user. Regardless of the type of notification message, although not shown in FIG. 7, the remote notification processing 700 could verify that the interested user is authorized to receive such a notification message before the notification message is sent 708 to the interested user. After the notification message has been sent 708 to the interested user, the remote notification processing 700 is complete and ends. Nevertheless, the remote notification processing 700 can continue periodically, on-demand or as the status information is updated.

Figure 8:
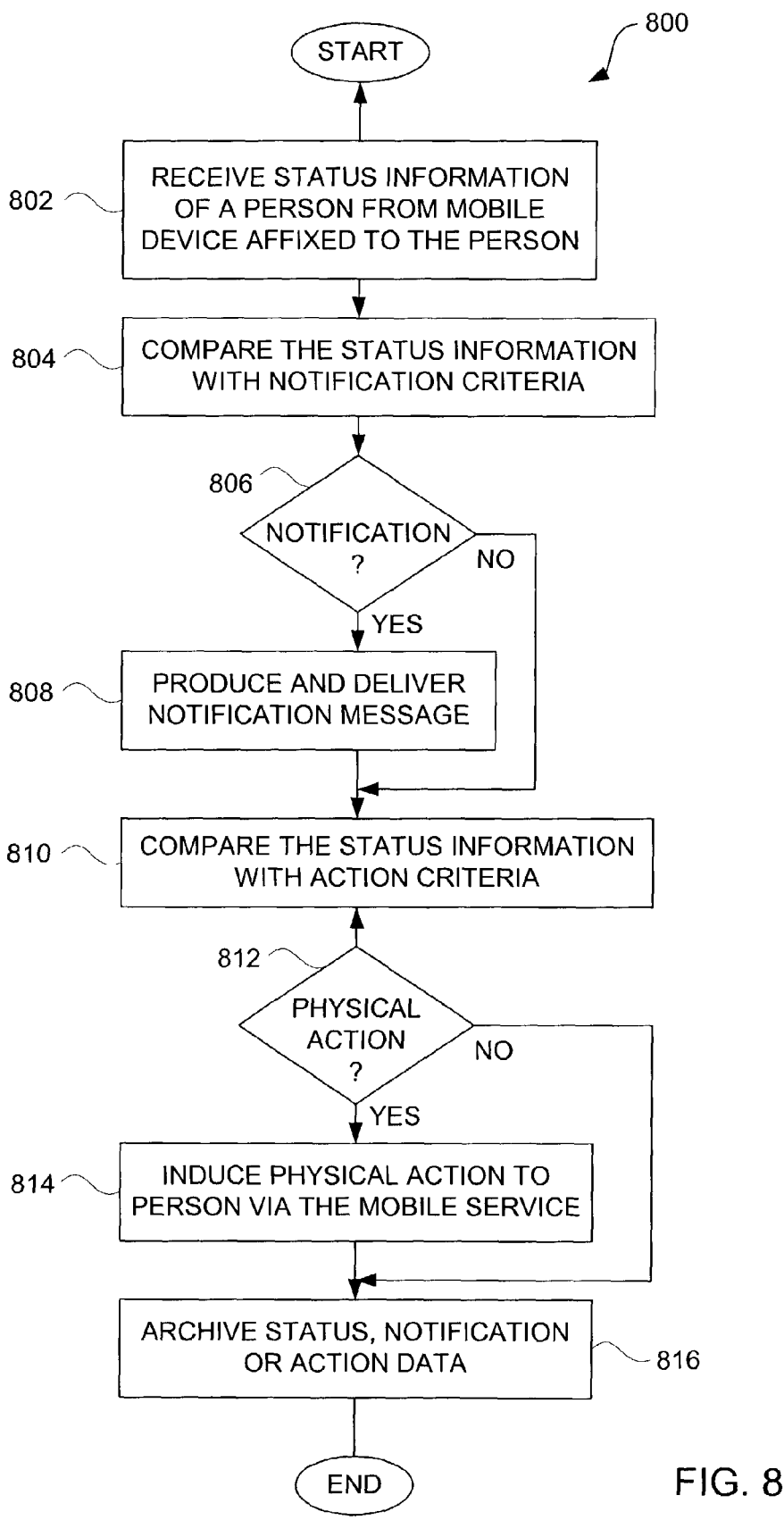
FIG. 8 is a flow diagram of notification and physical response processing according to one embodiment of the invention.

FIG. 8 is a flow diagram of notification and physical response processing 800 according to one embodiment of the invention. The notification and physical response processing 800 is, for example, performed by a medical monitoring device alone or with the assistance of a monitoring server.

The notification and physical response processing 800 receives 802 status information of a person. Typically, the status information of the person is provided by a medical monitoring device (affixed or coupled to the person). The status information that has been received 802 is then compared 804 with notification criteria. Here, according to one embodiment, the notification criteria can be specific to the person and/or can depend upon status information. In one embodiment, the particular notification criteria utilized is dependent upon the person and may be further dependent on the status information (e.g., type of status information). Next, a decision 806 determines whether a notification is needed. When the decision 806 determines that a notification is needed, then a notification message is produced and delivered 808. Alternatively, when the decision 806 determines that a notification is not needed, then the operation 808 is bypassed.

Besides the notification, the notification and physical response processing 800 can also induce a physical response to the person. Typically, the physical response would be induced to the person by the medical monitoring device affixed to the person. In this regard, the status information for the person is compared 810 with action criteria. Here, according to one embodiment, the action criteria can be specific to the person and/or can depend upon status information. The comparison 810 of the status information with the action criteria can also take into account a history of the status information for the person.

Next, a decision 812 determines whether a physical action should be induced. When the decision 812 determines that a physical action should be induced based on the comparison 810, then a physical action is induced 814 to the person via a device, which can be a mobile device. The type of physical action that is induced 814 can depend upon the capabilities of the mobile device. Examples of physical actions that can be induced 814 include introduction of insulin, drugs, and the like to the person. The introduction may be achieved through a needle, a patch, a device fabricated by micromachining techniques, and various others.

The physical actions can, for example, administer a dosage of medication to a person, such as performed through an actuator. This actuator can be a Micro-Electro-Mechanical System (MEMS) device fabricated using micromachining techniques. One advantage of a MEMS device is that the amount of dosage can be minute and automated. In one embodiment, the medical monitoring device can also simultaneously sense the status of the person while administering a small amount of medication. The medical monitoring device with an actuator can introduce (e.g., inject) an accurate amount of medication into the person. The amount introduced can depend on the medical condition as well as activity level of the person. The amount introduced can be furthered modified in view of the person's medical history. Since the dosage can be minute, and its effect simultaneously monitored, the possibility of over-dosage can be significantly decreased. As an example, a diabetic person could use a medical monitoring device with an actuator. The medical monitoring device senses a blood sugar level of the diabetic person, and introduces (e.g., injects) a controlled amount of insulin into the diabetic person's blood stream to stabilize it. The medical monitoring device can further determine the diabetic person's activity level and adjust the amount of insulin accordingly. In one embodiment, at least a portion of the medical monitoring device is attached to the person to be monitored (e.g., attached to the arm of the person, embedded within the person's body, etc.).

Alternatively, when the decision 812 determines that a physical action is not to be induced, then the operation 814 is bypassed. Following the operation 814 or its being bypassed, if desired, the notification and physical response processing 800 can archive 816 status, notification or action data such that subsequent analysis of the data can be performed. Also, the history of the medical condition and actions taken can be archived for later review. Following the operation 816, the notification and physical response processing 800 is complete and ends. Nevertheless, the notification and physical response processing 800 can continue periodically, on-demand or as the status information is updated.

Figure 9:
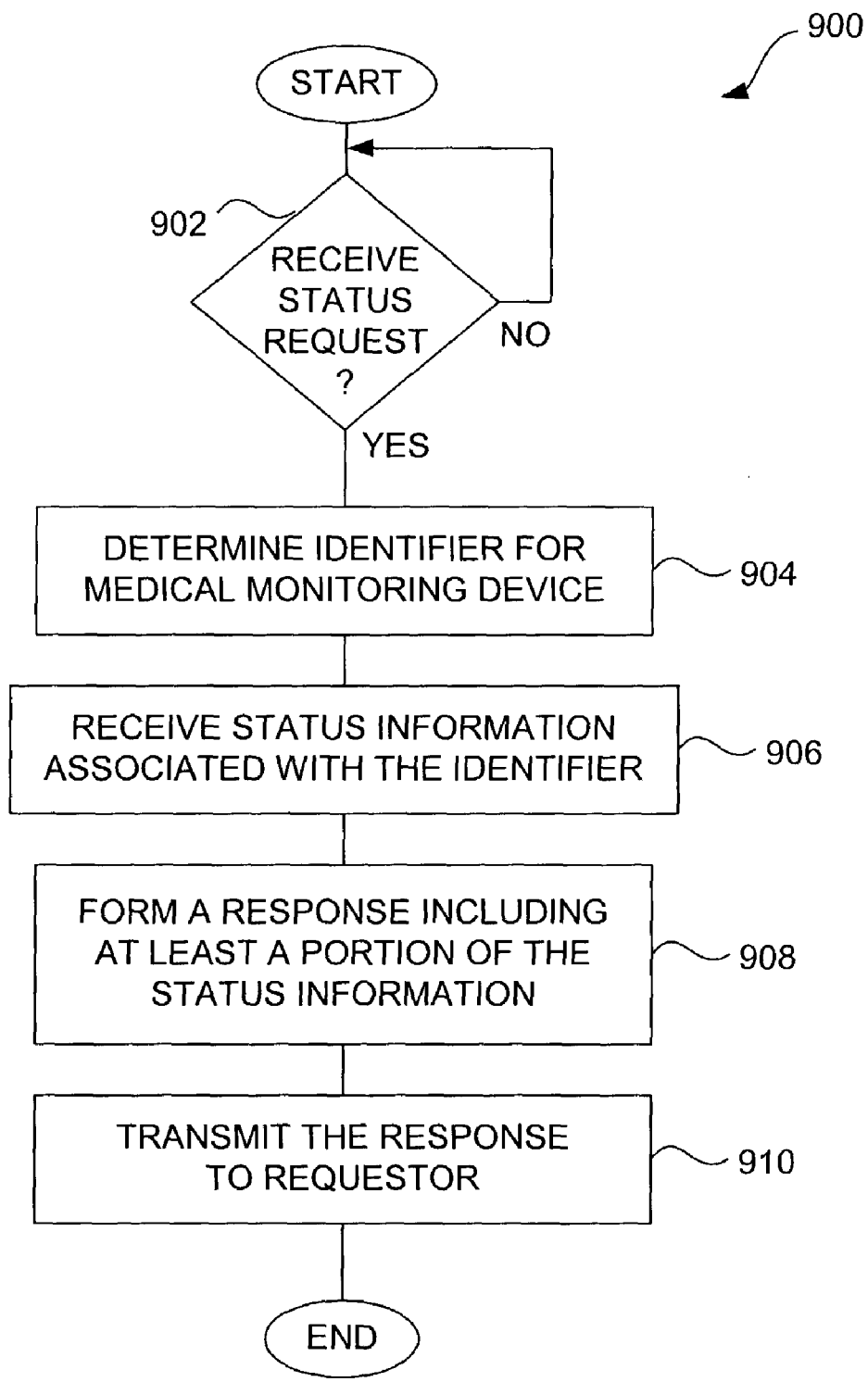
FIG. 9 is a flow diagram of requested notification processing according to one embodiment of the invention.

FIG. 9 is a flow diagram of requested notification processing 900 according to one embodiment of the invention. The requested notification processing 900 is, for example, performed by a server machine, such as the monitoring server 110 illustrated in FIG. 1.

The requested notification processing 900 begins with a decision 902 that determines whether a status request has been received. When the decision 902 determines that a status request has not been received, the requested notification processing 900 awaits such a request. In other words, the requested notification processing 900 can be considered to be invoked when a status request is received. A user (i.e., requestor) typically initiates the requested notification processing 900 when status information is desired by making a status request (or notification request). Typically, the user makes a status request by use of a client device associated with the user (i.e., requestor).

Once the decision 902 determines that a status request has been received, then an identifier for a medical monitoring device is determined 904. The identifier serves to identify the particular medical monitoring device for which the status information is to be obtained. After the identifier is identified, status information for the medical monitoring device associated with the identifier is retrieved 906. If desired, the requested notification processing 900 can further determine whether the requestor for the status information is authorized to receive the status information.

After the status information has been retrieved 906, a response including at least a portion of the status information is formed 908. In one embodiment, the response being formed 908 is in the format of an electronic mail (email) message (including any text or graphical message being electronically transmitted). For example, if the status request were in the form of an email message (including any text or graphical message being electronically transmitted), the response could be a reply email to the status request email message. In one implementation, the email message is an instant message, namely a near real time text message. In other embodiments, the response being formed 908 can take various other formats. After the response has been formed 908, the response is transmitted 910 to the requestor. The transmission of the response can be over a wireless and/or a wired network. For example, when the format of the response is an email message, the response is typically sent to a network address or email address associated with the requestor that issued the status request. Following the operation 910, the requested notification processing 900 is complete and ends.

Figure 10:
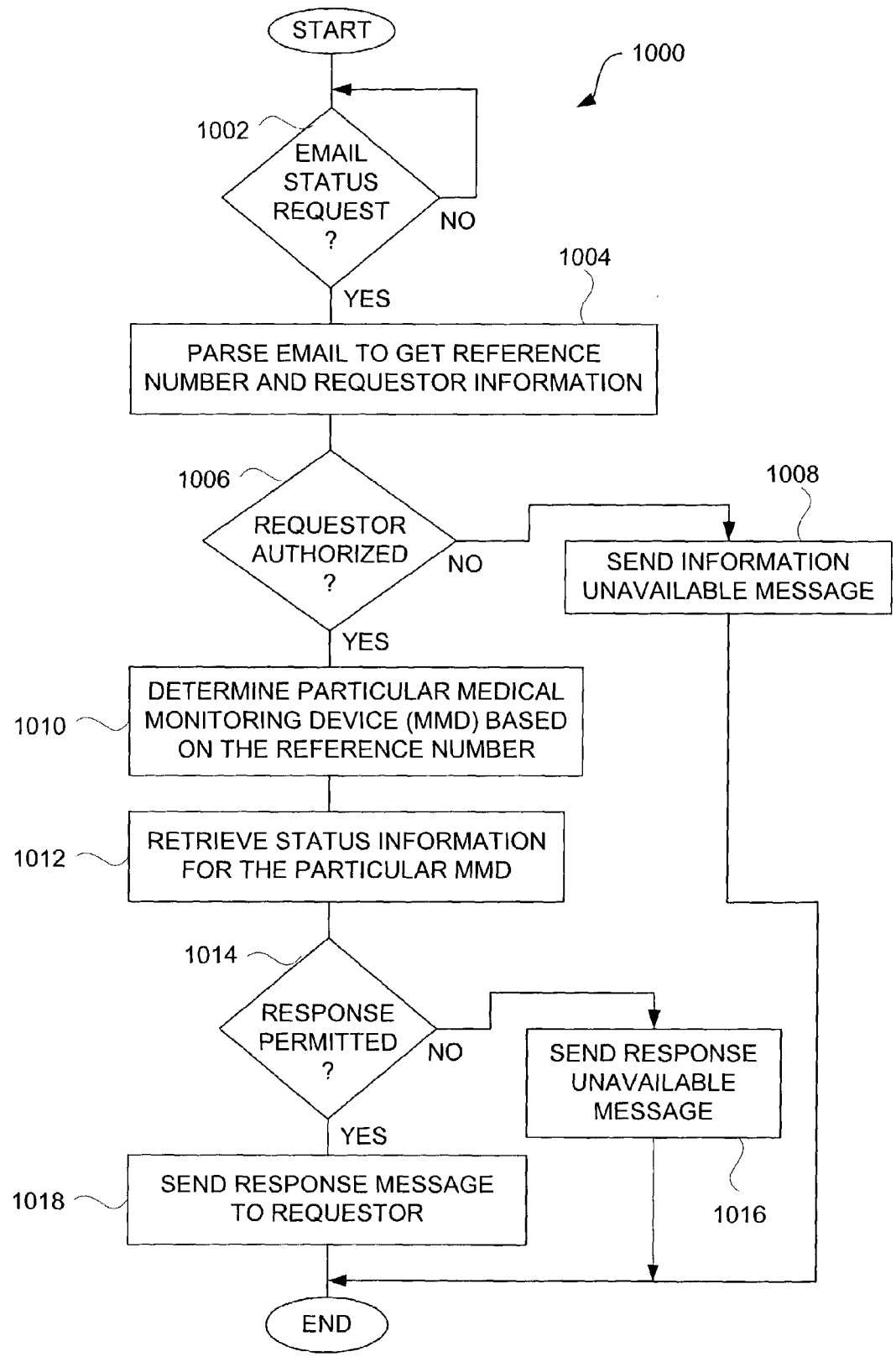
FIG. 10 is a flow diagram of email status processing according to one embodiment of the invention.

FIG. 10 is a flow diagram of email status processing 1000 according to one embodiment of the invention. The email status processing 1000 is, for example, performed by a server machine, such as the monitoring server 110 illustrated in FIG. 1. The email status processing 1000 can be considered a more detailed embodiment of the requested notification processing 900 illustrated in FIG. 9.

The email status processing 1000 begins with a decision 1002 that determines whether an email status request has been received 1002 from a requestor. When the decision 1002 determines that an email status request has not been received, then the email status processing 1000 awaits such a request. Once the decision 1002 determines that an email status request has been received, then the email status request can be parsed 1004 to get a reference number and requestor information.

Next, a decision 1006 determines whether the requestor is authorized. Here, the determination of whether or not the requestor is authorized can be performed using some or all of the requestor information and the reference number for the medical monitoring device of interest. When the decision 1006 determines that the requestor is not authorized, then an information unavailable message is sent 1008 to the requestor.

When the decision 1006 determines that the requestor is authorized, the medical monitoring device is determined 1010 based on the reference number. As an example, the reference number can be an identifier that is used by users to identify the medical monitoring device they are desirous of tracking. Internally the system may use the reference number or another identifier. The reference number may be a fixed number or a re-assignable number that specifies a particular medical monitoring device. For example, the reference number can be a telephone number or network address used by the medical monitoring device for communications.

After the medical monitoring device has been determined 1010, the status information for the determined medical monitoring device is retrieved 1012. In one embodiment, the status information is retrieved 1012 from a database that stores status information for a plurality of medical monitoring devices or the persons having the medical monitoring devices affixed thereto. The database is, for example, the tracking database 116 illustrated in FIG. 1.

Next, a decision 1014 determines whether the requested response is permitted. In other words, although the requestor is permitted to access the status information, the type (e.g., format or content) of response that is permitted to be supplied to the requestor could be limited. Hence, when the decision 1014 determines that the requested response is not permitted, then a requested response unavailable message is sent 1016 to the requestor. On the other hand, when the decision 1014 determines that the requested response is permitted, then a response message is produced and sent 1018 to the requestor. In one embodiment, the message can take different formats or content depending upon a user's configuration request, a requestor's authorization level, or the destination for the response message. Following the operation 1018, as well as following the operations 1008 and 1016, the email status processing 1000 ends.

A web interface (or Graphical User Interface) can be made available to users. The web interface can, among other things, assist a user with configuring is notifications for themselves or others. One embodiment of such a web interface is referred to as a notification setup screen. A web interface could also be used to allow a requestor to view requested status information.

The position resolution can be enhanced through use of a community layout and/or localized profile information.

Figure 11:
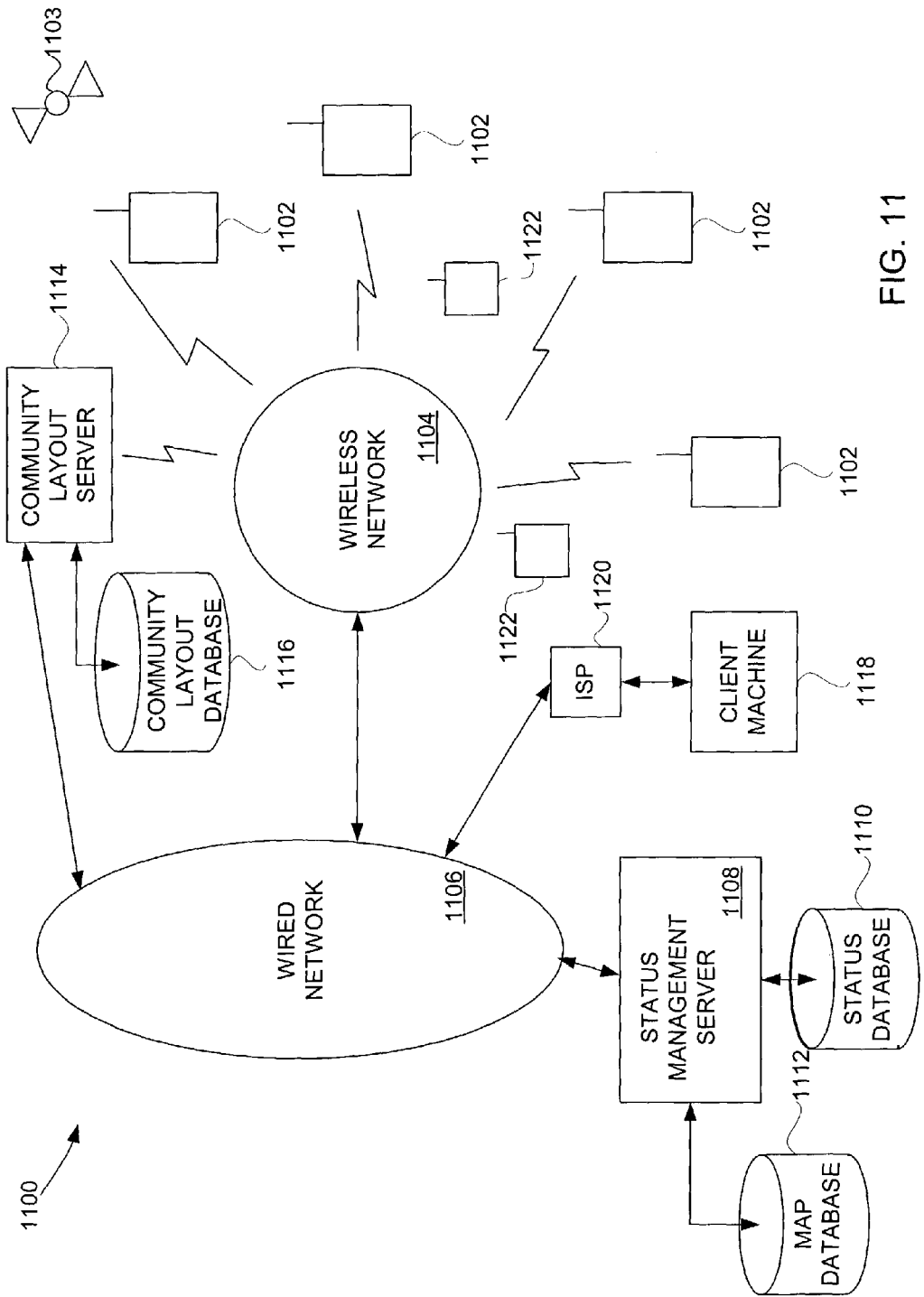
FIG. 11 is a block diagram of an object monitoring system according to one embodiment of the invention.

FIG. 11 is a block diagram of a monitoring system 1100 according to one embodiment of the invention. The monitoring system 1100 can be used to monitor medical conditions of beings, such as humans and/or pets (users). The monitoring system 1100 includes a plurality of mobile devices 1102. These mobile devices 1102 are provided with, affixed to or proximate to users being tracked by the monitoring system 1100. These mobile devices 1102 can have GPS receivers that can receive GPS position information from a GPS system 1103. The mobile devices 1102 also receive health information from sensors as noted above for medical monitoring devices. The acquisition of such position or health information can be performed on demand, periodically or on need. The mobile devices 1102 communicate over wireless links with a wireless network 1104. The wireless network 1104 then couples to a wired network 1106. A status management server 1108 is coupled to the wireless network 1106. The status management server 1108 provides centralized storage of status information (e.g., health information, location information and possibly other information) for each of the mobile devices 1102 or its users in a status database 1110. A map database 1112 is also coupled to the status management server 1108. The map database 1112 can directly connect to the status management server 1108 or can reside elsewhere on the wired network 1106. The status management server 1108 can interact with the map database 1112 to convert position information provided by the GPS information into map coordinates, street addresses, etc.

In addition, the object monitoring system 1100 also includes a community layout server 1114. The community layout server 1114 can be coupled to the wired network 1106 or the wireless network 1104. In one embodiment, a community can be associated with a commercial building, a shopping mall, a residential community and the like. The community layout server 1114 interacts with a community layout database 1116 to resolve locations, such as street addresses, cross streets or longitude and latitude, into precise locations in a community. For example, the precise locations can pertain to points of interest with respect to the community. As an illustration, in the case of a commercial building, with five floors, the community layout database 1116 would convert the GPS information (plus any additional sensor information relevant to making the determination may also be provided by the mobile device 1102, such as altitude and direction) to obtain a community location or point of interest. For example, using the GPS position information together with other sensor information, the community layout server 1114 can interact with the community layout database 1116 to precisely locate a particular mobile device 1102 to a particular point of interest. For example, in the case of the commercial building with five floors, the mobile device 1102 can be pinpointed to the third floor which pertains to the corporation Acme, Inc. The point of interest or community position can then be sent from the community layout server 1114 through the wired network 1106 to the location management server 1108 which then in turn stores the community position or point of interest in the status database 1110 as the position of the particular mobile device 1102.

Once the status database 1110 has the positions of the mobile devices 1102, when subsequent position data is sent to the status management server 1108, these positions are suitably updated in the status database 1110. Additionally, other of the mobile devices 1102 or a representative client machine 1118 coupled through an Internet Service Provider (ISP) 1120 to the wired network 1106 can be permitted to access the status of one or more of the mobile devices 1102. Assuming that the requesting party is allowed access to status information, the request for such information is processed by the status management server 1108. When permission is granted, the status desired is retrieved from the status database 1110 and returned to either the requesting mobile devices 1102 or the requesting client machine 1118.

In one embodiment, the client machine 1118 or a particular one of the mobile devices 1102, or users thereof, can set up a private or semi-private web page that is hosted by a server (e.g., the status management server 1108 or other server) on the wired network 1106. Then, the page can be customized to monitor the status of a number of the mobile devices 1102 (namely, the persons affixed thereto). Hence, thereafter, the requestor need only access the customized web page to obtain the current status information for such mobile devices. With such an embodiment, a web page could be provided to monitor one or more persons. In another embodiment, a similar web page can be setup to allow a user to track the status of mobile devices that are affixed to, for example, his elderly parents. This would allow the requestor (interested person) to easily monitor the status (e.g., medical information and/or location information) of, for example, his parents.

The monitoring system 1100 could also be augmented by wireless profile devices 1122. These profile devices 1122 can wirelessly couple to the mobile devices 1102 using the wireless network 1104. The profile devices 1122 could be short range transmitters or transceivers. The profile devices 1122 could store one or more profiles for a particular location in which they reside.

Hence, the mobile device 1102 can wirelessly communicate with the profile device 1122, if available, to acquire a profile pertaining to its location. For example, with the profile device 1122 placed in the office building of Acme, Inc., when the mobile device 1102 is in such office building, the mobile device 1102 can acquire the profile from the profile device 1122 that is proximate to the mobile device 1102. The profile can include the business name, its location, contact information for the business, etc. Thereafter, some or all of the profile information can be stored in the mobile device 1102 and/or forwarded to the status management server 1108 or other server for storage. Hence, the location provided by the profile may be more exacting and descriptive than the GPS position, such that the location of the mobile device 1102 can be better determined.

In some cases it may be useful to control or limit the wireless communications with respect to the profile devices 1122 so that the mobile devices 1102 do not inadvertently receive the wrong profile. Various techniques can be utilized to provide control over the wireless communications. For example, the profile device 1122 may or may not use a directional antenna. As another example, the profile device 1122 could also control (e.g., limit) its transmission power so that its profile information can only be received by devices within a certain distance.

In still another embodiment, personalized medical monitoring can be provided. For example, a user can monitor themselves or a user can monitor another person as they desire. Such monitoring can be achieved independent of a medical facility.

A representative scenario is as follows. A user acquires a status-aware mobile communication device, such as a medical monitoring device, and affixes the mobile communication device to the person to be monitored. The user makes note of the identifier for the mobile communication device and the person being monitored. Then, periodically or on-demand, the user can determine the status of the monitored person. In one implementation, the user (or a server on the user's behalf) sends a message to the mobile communication device. The message can be a voice or text message that simply requests the mobile communication device to get its present status. The mobile communication device then determines status data being requested. The request can be for the health condition of the person being monitored through use of sensors of the mobile communication device. The mobile communication device can determine its location, for example, by directly using a GPS receiver or indirectly via a hub device having GPS awareness. Further, battery lifetime can be conserved using the intelligent GPS information acquisition approaches as, for example, noted in U.S. Provisional Patent Application No. 60/375,998. The mobile communication device then replies back (e.g., through voice or text message) to the user (or server) to inform of the status of the monitored person. The user can, for example, call or page the mobile communication device and get the status data in a reply message. Alternatively, the user needs only access a server to retrieve the status data it holds for the person being monitored. The server can also automatically monitor these mobile communication devices and notify or alert users (e.g., the monitored person or interested party) when problems or dangerous conditions are identified. Besides health conditions and location, reply messages could also provide other information back such as velocity, temperature, humidity, pressure, forces or stresses.

In one embodiment, the mobile device (mobile communication device) can include a solar panel. The solar panel can provide electrical power for the mobile device. The solar panel can thus charge a battery used to power the mobile device and/or itself power the mobile device. When the mobile device is affixed to a person to be monitored, the solar panel can remain at least partially exposed to the outside environment so as to be able to receive light. The solar panel can be integrated with the housing of the mobile device or can be separate and coupled to the mobile device via one or more wires (e.g., a cable).

The present invention has described one or more GPS devices as to identify a location. However, the present invention is not limited to using GPS devices. In certain situations, other wireless or mobile devices can also serve as location-designating devices, such as devices based on GSM technologies, Bluetooth or Wi-Fi technologies. Through the techniques of triangulation, these devices can also designate a location. Such triangulation techniques should be known to those skilled in the art.

Although the invention has been described above in the context of monitoring persons, the invention can likewise be used to monitor animals (e.g., pets) or other living beings.

The above-described systems, devices, methods and processes can be used together with other aspects of a monitoring system, including the various aspects described in: (i) U.S. Provisional Patent Application No. 60/444,198, filed Jan. 30, 2003, and entitled "SYSTEM, METHOD AND APPARATUS FOR ACQUIRING, to PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

The invention can be implemented in software, hardware or a combination of hardware and software. The invention can also be embodied as computer readable code on a computer readable medium. The computer readable medium is any data storage device that can store data which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

The advantages of the invention are numerous. Different embodiments or implementations may yield different advantages. One advantage of the invention is that a person's health can be monitored with a portable medical monitoring system. Another advantage of the invention is that portable medical monitoring systems can be low cost and utilized without assistance of medical professionals or trained technicians. Still another advantage of the invention is that status information of a person being monitored can be obtained by an interested party through notifications or through access to a website (e.g., monitoring server). Yet another advantage of the invention is that notifications, recommendations and/or actions can be initiated by examination or analysis of the status information.

The many features and advantages of the present invention are apparent from the written description and, thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

What is claimed is:

1. A method for monitoring status of a person, said method being performed at least in part by a monitoring server, said method comprising:
    acquiring status information of the person being monitored, the status information being acquired using at least one electronic device, and the status information including at least health information of the person;
    obtaining at least a first threshold condition and a second threshold condition for use in monitoring the person;
    determining, at the monitoring server, whether an action condition exists by comparing the health information with at least one or both of the first threshold condition and the second threshold condition; and
    initiating an action when said determining determines that the action condition exists,
    wherein the action includes sending a notification to at least one recipient,
    wherein the status information further includes location information of the person being monitored, and
    wherein at least the first threshold condition is dependent on the location information of the person being monitored, such that the first threshold condition is set to a first level when the person is at a first location, and the first threshold condition is set to a second level when the person is at a second location.

2. A method as recited in claim 1, wherein the notification advises the person to compensate for a physical condition of the person.

3. A method as recited in claim 1, wherein said acquiring of the status information of the person being monitored is periodically performed.

4. A method as recited in claim 1, wherein said acquiring of the status information of the person being monitored is performed in real-time.

5. A method as recited in claim 1, wherein the at least one recipient is enabled through a web interface to configure at least one attribute of the notification to be sent.

6. A method as recited in claim 1, wherein the health information is acquired using at least one sensor.

7. A method as recited in claim 1, wherein at least one of the first threshold condition and the second threshold condition is configurable.

8. A method as recited in claim 7, wherein the location information is based on location data acquired using a GPS receiver.

9. A method as recited in claim 1, wherein at least one of the first threshold condition and the second threshold condition is personal to and able to be adjusted by the person.

10. A method as recited in claim 1, wherein the location information is based on location data acquired using a GPS receiver.

11. A method as recited in claim 10, wherein the at least one recipient is enabled through a web interface to configure at least one attribute of the notification to be sent.

12. A method as recited in claim 1, wherein the notification is an electronic message.

13. A method as recited in claim 1, wherein the at least one electronic device is a wearable device.

14. A method as recited in claim 13, wherein at least one of the first threshold condition and the second threshold condition is configurable, and wherein the location information is based on location data acquired using a GPS receiver.

15. A method as recited in claim 14, wherein the health information is acquired using at least one sensor.

16. A method as recited in claim 1, wherein the at least one electronic device is a status-aware mobile device that is adapted to be affixed to the person, and wherein said acquiring of the status information of the person being monitored is provided by at least one sensor of the status-aware mobile device.

17. A method for monitoring status of a person, said method being performed at least in part by a monitoring server, said method comprising:
    acquiring status information of the person being monitored, the status information being acquired using at least one electronic device, and the status information including at least health information of the person;
    obtaining at least one threshold condition to be applied;
    determining, at the monitoring server, whether an action condition exists by comparing the health information with at least the at least one threshold condition; and
    initiating an action when said determining determines that the action condition exists,
    wherein the status information further includes at least location information pertaining to the person,
    wherein said obtaining of the at least one threshold condition comprises:
        determining an activity associated with the person; and
        determining the at least one threshold condition based on the activity associated with the person, the at least one threshold condition being determined is set to a first level when the person is engaging in a first activity and is set to a second level when the person is engaging in a second activity, and
    wherein said determining of the activity associated with the person is based on at least the location information pertaining to the person.

18. A method as recited in claim 17, wherein the at least one electronic device is a status-aware mobile device that is adapted to be affixed to the person, and wherein said acquiring of the status information of the person being monitored is provided by the status-aware mobile device.

19. A method as recited in claim 18, wherein said acquiring transmits the status information from the status-aware mobile device to the monitoring server over at least a part of a wireless network.

20. A method as recited in claim 19, wherein the monitoring server stores a plurality of threshold conditions respectively corresponding to a plurality of persons or status-aware mobile devices.

21. A method as recited in claim 18, wherein the status-aware mobile device is a wearable device.

22. A method as recited in claim 17, wherein the action depends on a piece of demographic information of the person.

23. A method as recited in claim 17, wherein the action depends on a piece of status information of the person that was previously acquired.

24. A method as recited in claim 17, wherein the action is related to a medication dosage, and wherein the medication is administered by a device fabricated using micromachining techniques.

25. A method as recited in claim 17, wherein the action is a medication dosage, and wherein the medication dosage is adjusted based on a subsequent piece of the status information.

26. A method as recited in claim 17, wherein the location information includes a location of the person being monitored, wherein said method comprises generating a notification that directs the person to another location for health reasons, and wherein the another location is determined depending on the location of the person.

27. A method as recited in claim 17, wherein the threshold condition is configurable.

28. A method for monitoring status of a person, said method comprising:
   acquiring status information of the person being monitored, the status information being acquired using at least one electronic device, and the status information including at least health information of the person;
   obtaining at least one threshold condition to be applied;
   determining whether an action condition exists by comparing the health information with at least the at least one threshold condition; and
   initiating an action when said determining determines that the action condition exists,
   wherein the status information further includes at least location information pertaining to the person,
   wherein said obtaining of the at least one threshold condition comprises:
      determining an activity associated with the person; and
      determining the at least one threshold condition based on the activity associated with the person, the at least one threshold condition being determined is set to a first level when the person is engaging in a first activity and is set to a second level when the person is engaging in a second activity, and
   wherein said determining of the activity associated with the person is based on at least the location information pertaining to the person, and
   wherein the action includes an electronic mail notification sent to at least one recipient, and wherein the at least one recipient is enabled through a web interface to configure when and/or how the notification is to be sent.

29. A method for monitoring status of a person, said method being performed at least in part by a monitoring server, said method comprising:
   receiving status information of a person being monitored, the status information being provided by a status-aware mobile device adapted to be affixed to the person, the status information including at least a location of the status-aware mobile device and a health condition of the person;
   obtaining at least one threshold condition to be applied, the at least one threshold condition being able to be influenced by or for the person;
   determining, at the monitoring server, whether a notification should be provided to the person based on at least the health condition of the person and the at least one threshold condition;
   generating a notification based on the location and the health condition if said determining has determined that a notification should be provided; and
   providing the notification to the person,
   wherein the at least one threshold condition is dependent on an activity associated with the person, such that the at least one threshold condition used by said determining is set to a first level when the person is engaging in a first activity, and the at least one threshold condition is set to a second level when the person is engaging in a second activity, and
   wherein the activity associated with the person is based on at least the location of the status-aware mobile device.

30. A method as recited in claim 29, wherein the at least one threshold condition is dependent on the location of the status-aware mobile device adapted to be affixed to the person, such that the at least one threshold condition used by said determining is set to a first level when the status-aware mobile device is at a first location, and the at least one threshold condition is set to a second level when the status-aware mobile device is at a second location.

31. A method as recited in claim 29, wherein the at least one threshold condition is dependent on the location of the status-aware mobile device adapted to be affixed to the person.

32. A method for monitoring status of a person, said method comprising:
   receiving status information of a person being monitored, the status information being provided by a status-aware mobile device adapted to be affixed to the person, the status information including at least a location of the status-aware mobile device and a health condition of the person;
   obtaining at least one threshold condition to be applied, the at least one threshold condition being able to be influenced by or for the person;
   determining whether a notification should be provided to the person based on at least the health condition of the person and the at least one threshold condition;
   generating a notification based on the location and the health condition if said determining has determined that a notification should be provided; and
   providing the notification to the person,
   wherein the at least one threshold condition is dependent on an activity associated with the person, such that the at least one threshold condition used by said determining is set to a first level when the person is engaging in a first activity, and the at least one threshold condition is set to a second level when the person is engaging in a second activity, and
   wherein the activity associated with the person is based on at least the location of the status-aware mobile device, and
   wherein said providing of the notification causes an electronic mail notification to be sent to at least one recipient and the notification includes at least a portion of the status information.

33. A method for monitoring status of a person, said method being performed at least in part by a monitoring server, said method comprising:
- acquiring status information of the person being monitored, the status information being acquired using at least one electronic device, and the status information including at least health information of the person, the health information including at least first health condition data provided by a first sensor and second health condition data provided by a second sensor;
- obtaining at least a first threshold condition for use with respect to the first health condition data;
- obtaining at least a second threshold condition for use with respect to the second health condition data;
- determining, at the monitoring server, whether an action condition exists based on (i) comparing the first health condition data to the first threshold condition, and/or (ii) comparing the second health condition data to the second threshold condition; and
- initiating an action when said determining determines that the action condition exists,
- wherein the action includes sending a notification to at least one recipient if the action condition is determined to exist,
- wherein the status information further includes location information of the person being monitored, and
- wherein at least the first threshold condition is dependent on the location information of the person being monitored.

34. A method as recited in claim 33, wherein the first threshold condition is configurable for the person by either the person or the at least one recipient.

35. A method as recited in claim 33, wherein the first threshold condition is set to a first level when the person is at a first location, and the first threshold condition is set to a second level when the person is at a second location.

36. A method as recited in claim 33, wherein the at least one recipient is enabled through a web interface to configure when and/or how the notification is to be sent.

37. A method as recited in claim 33, wherein the at least one electronic device is a status-aware mobile device that is adapted to be affixed at or proximate to the person, and wherein said acquiring of the status information of the person being monitored is provided by the status-aware mobile device.

38. A method as recited in claim 37, wherein said method is performed by a remote server, and
- wherein, in providing the status information to the remote server, said acquiring of the status information comprises transmitting the status information from the status-aware mobile device to the remote server over at least a part of a wireless network.

39. A method as recited in claim 38, wherein the remote server stores a plurality of threshold conditions respectively corresponding to a plurality of persons or status-aware mobile devices.

* * * * *

UNITED STATES PATENT AND TRADEMARK OFFICE
CERTIFICATE OF CORRECTION

PATENT NO.         : 7,905,832 B1                                         Page 1 of 1
APPLICATION NO.    : 10/397641
DATED              : March 15, 2011
INVENTOR(S)        : Lau et al.

It is certified that error appears in the above-identified patent and that said Letters Patent is hereby corrected as shown below:

In the Cover Page(s), References Cited, Section (56):
    Page 2, right column, line 25 "Planca et al." should be --Pianca et al.--
    Page 2, right column, line 52 "Planca et al." should be --Pianca et al.--

In the Specification:
    Column 13, line 43 "is notifications" should be --notifications--.
    Column 16, line 36 "to PRESENTING," should be --PRESENTING,--.

Signed and Sealed this
Twenty-second Day of November, 2011

David J. Kappos
*Director of the United States Patent and Trademark Office*